(12) United States Patent
Satoh et al.

(10) Patent No.: US 8,403,669 B2
(45) Date of Patent: Mar. 26, 2013

(54) ARTIFICIAL TOOTH

(75) Inventors: Hirokazu Satoh, Kyoto (JP); Noriyuki Negoro, Kyoto (JP); Kunihiro Fujii, Kyoto (JP)

(73) Assignee: Kabushiki Kaisha Shofu, Kyoto (JP)

( * ) Notice: Subject to any disclaimer, the term of this patent is extended or adjusted under 35 U.S.C. 154(b) by 0 days.

(21) Appl. No.: 12/596,437

(22) PCT Filed: Apr. 18, 2007

(86) PCT No.: PCT/JP2007/058423
§ 371 (c)(1),
(2), (4) Date: Oct. 17, 2009

(87) PCT Pub. No.: WO2008/129673
PCT Pub. Date: Oct. 30, 2008

(65) Prior Publication Data
US 2010/0119992 A1 May 13, 2010

(51) Int. Cl.
*A61C 13/00* (2006.01)
(52) U.S. Cl. ..................... 433/199.1; 433/197
(58) Field of Classification Search .......... 433/199.1, 433/201.1, 171, 214
See application file for complete search history.

(56) References Cited

U.S. PATENT DOCUMENTS

| 943,113 | A | | 12/1909 | Greenfield | |
|---|---|---|---|---|---|
| 2,006,717 | A | * | 7/1935 | Phillips | 433/197 |
| 2,095,432 | A | * | 10/1937 | Brenner | 433/197 |
| 2,104,459 | A | * | 1/1938 | Gysi | 433/197 |
| D114,512 | S | | 4/1939 | Settell | |
| 2,585,857 | A | | 2/1952 | Schwartz | |
| 2,874,832 | A | | 2/1959 | Gordon | |
| 3,247,844 | A | | 4/1966 | Berghash | |
| 3,423,831 | A | | 1/1969 | Semmelman | |
| D272,465 | S | | 1/1984 | Wolf | |
| 4,445,863 | A | * | 5/1984 | Lang et al. | 433/212.1 |
| 4,481,162 | A | | 11/1984 | Huffman | |
| 4,523,912 | A | | 6/1985 | Breustedt et al. | |
| 4,872,840 | A | | 10/1989 | Bori | |
| 4,911,641 | A | | 3/1990 | Detsch | |
| 4,969,817 | A | | 11/1990 | Hiranuma et al. | |
| 4,997,373 | A | | 3/1991 | Tanaka et al. | |
| 5,051,091 | A | | 9/1991 | Rosenfeld | |
| 5,232,370 | A | | 8/1993 | Hoye | |
| 5,234,339 | A | | 8/1993 | Grigereit | |

(Continued)

FOREIGN PATENT DOCUMENTS

DE 4432176 A1 3/1996
DE 19508762 C1 5/1996
(Continued)

OTHER PUBLICATIONS

Toshio Hayashi et al., Complete Denture Prosthetics, Ishiyaku Pub. Inc., Apr. 10, 1982, pp. 309-311.

(Continued)

*Primary Examiner* — Cris L Rodriguez
*Assistant Examiner* — Matthew Saunders
(74) *Attorney, Agent, or Firm* — Capitol City TechLaw

(57) ABSTRACT

Artificial teeth of upper and lower jaws, allowing easy operation by clarifying the three-dimensional positional relation of cusp tips and pits to contact with each other in occlusion. Each pair of artificial teeth may include cusp tips and pits, and the positional relation of the cusp tips and pits are set appropriately.

8 Claims, 15 Drawing Sheets

U.S. PATENT DOCUMENTS

| | | | |
|---|---|---|---|
| 5,733,125 A * | 3/1998 | Foser | 433/197 |
| 5,788,489 A | 8/1998 | Huffman | |
| 5,788,490 A | 8/1998 | Huffman | |
| 5,906,489 A | 5/1999 | Khazzam et al. | |
| 5,951,289 A * | 9/1999 | Kura et al. | 433/202.1 |
| 6,394,810 B1 | 5/2002 | Choi | |
| 6,431,868 B2 | 8/2002 | Story | |
| 6,488,503 B1 | 12/2002 | Lichkus et al. | |
| 6,533,581 B1 * | 3/2003 | Moenckmeyer | 433/197 |
| 6,790,035 B2 | 9/2004 | Tricca et al. | |
| 6,935,861 B2 * | 8/2005 | Lauciello | 433/197 |
| 7,059,850 B1 | 6/2006 | Phan et al. | |
| 7,108,511 B1 | 9/2006 | Shatkin | |
| 7,201,576 B2 | 4/2007 | Tricca et al. | |
| 7,267,549 B2 * | 9/2007 | Monkmeyer | 433/197 |
| 7,699,610 B2 | 4/2010 | Childress | |
| 2003/0031981 A1 | 2/2003 | Holt | |
| 2005/0095559 A1 | 5/2005 | Monkmeyer | |
| 2006/0263749 A1 | 11/2006 | Koide | |
| 2010/0266988 A1 | 10/2010 | Satoh et al. | |

FOREIGN PATENT DOCUMENTS

| | | | |
|---|---|---|---|
| GB | 2433444 A | | 6/2007 |
| JP | D777064 | | 12/1989 |
| JP | D7770641 | | 4/1990 |
| JP | 08-112294 A | | 5/1996 |
| JP | 10-504985 A | | 5/1998 |
| JP | 11-290347 A | | 10/1999 |
| JP | 11290347 A | * | 10/1999 |
| JP | 2002-177301 A | | 6/2002 |
| JP | 2002177301 A | * | 6/2002 |
| JP | 2002523134 A | | 7/2002 |
| JP | 2003-102752 A | | 4/2003 |
| JP | 2003102752 A | * | 4/2003 |
| JP | 2003135489 A | * | 5/2003 |
| JP | D1197057 | | 2/2004 |
| JP | D1197058 | | 2/2004 |
| JP | D1197530 | | 2/2004 |
| JP | D1202523 | | 4/2004 |
| JP | D1202524 | | 4/2004 |
| JP | D1203086 | | 4/2004 |
| JP | D1203087 | | 4/2004 |
| JP | D1203088 | | 4/2004 |
| JP | D1203089 | | 4/2004 |
| JP | D1203090 | | 4/2004 |
| JP | D1203091 | | 4/2004 |
| JP | 2005525841 A | | 9/2005 |
| JP | 3747251 B2 | | 2/2006 |
| WO | WO 96/07365 A1 | | 3/1996 |
| WO | WO 9607365 A1 | * | 3/1996 |

OTHER PUBLICATIONS

Hiromichi Tsuru et al., Complete Denture Technique, Third Edition, Ishiyaku Pub. Inc., Oct. 30, 1993, pp. 141-143.

S.S. White's Dental Catalog, 1876, pp. 22-23, Figs. 4 through 7, illustrations of artificial teeth from the side profile.

The S.S. White Dental Mfg. Co. Catalog, 1890, p. 84, Figs. 2 and 3 showing an artificial tooth with dimple and mounting pin.

The S.S. White Dental Mfg. Co. Crown and Bridge Works Catalog, 1899, p. 108, Hollingsworth's crown and bridge work system Set Nos. 1 and 2.

S.S. White Dental Mfg. Co., Operative Instruments and Accessories. Catalog "F", 1907, p. 76, Fig. 8 showing artificial teeth with dimple area for mounting pin.

Oxford University of Natural History/The Learning Zone. Upper and Lower teeth. Copyright 2006.

Yeti Dental Flier, 1994/95, p. 30 showing images of artificial molars at the bottom of the page.

Shofu Inc., Veracia SA Anterior and Posterior Q-Pack brochure, published Mar. 2011.

* cited by examiner

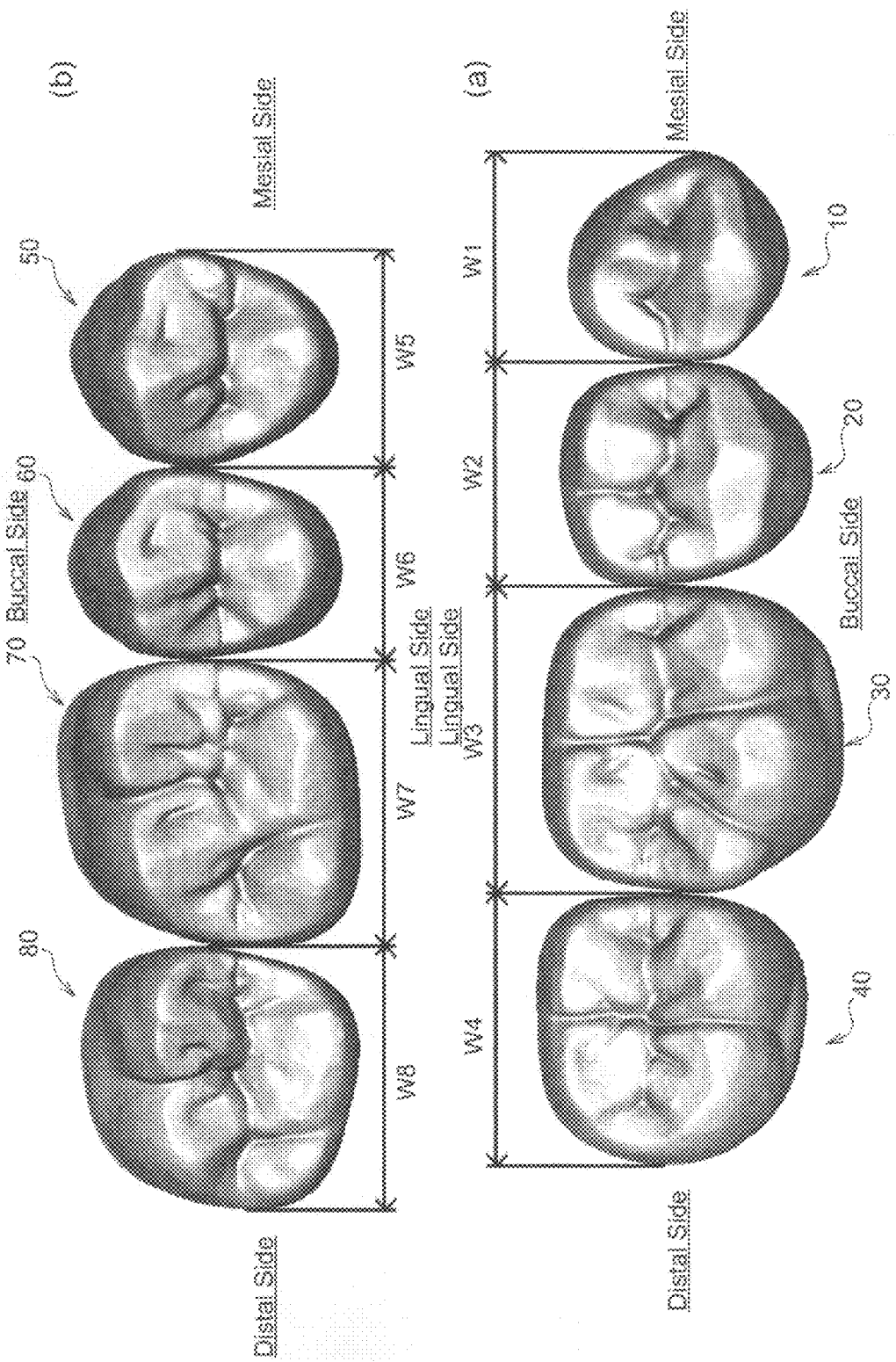

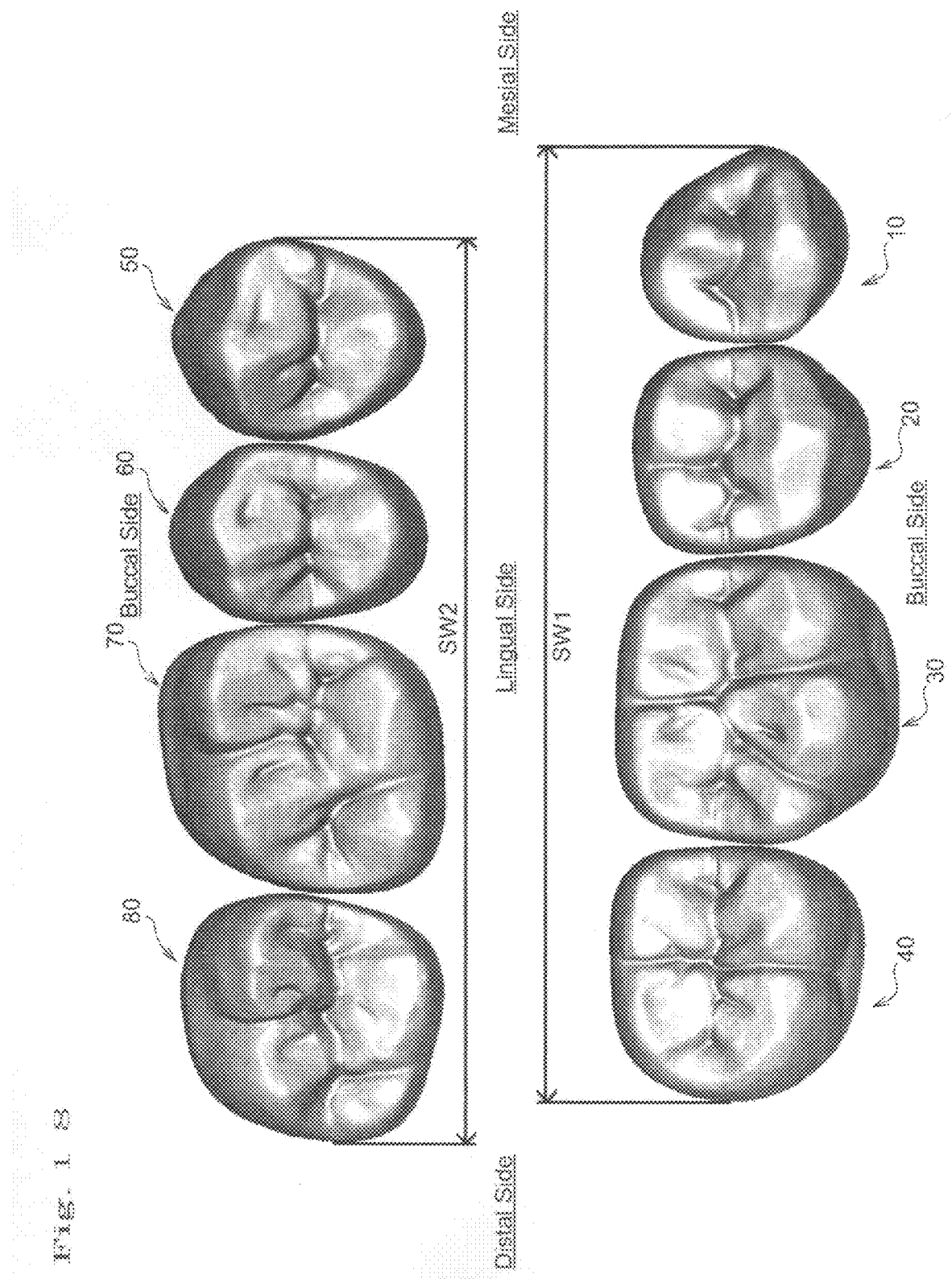

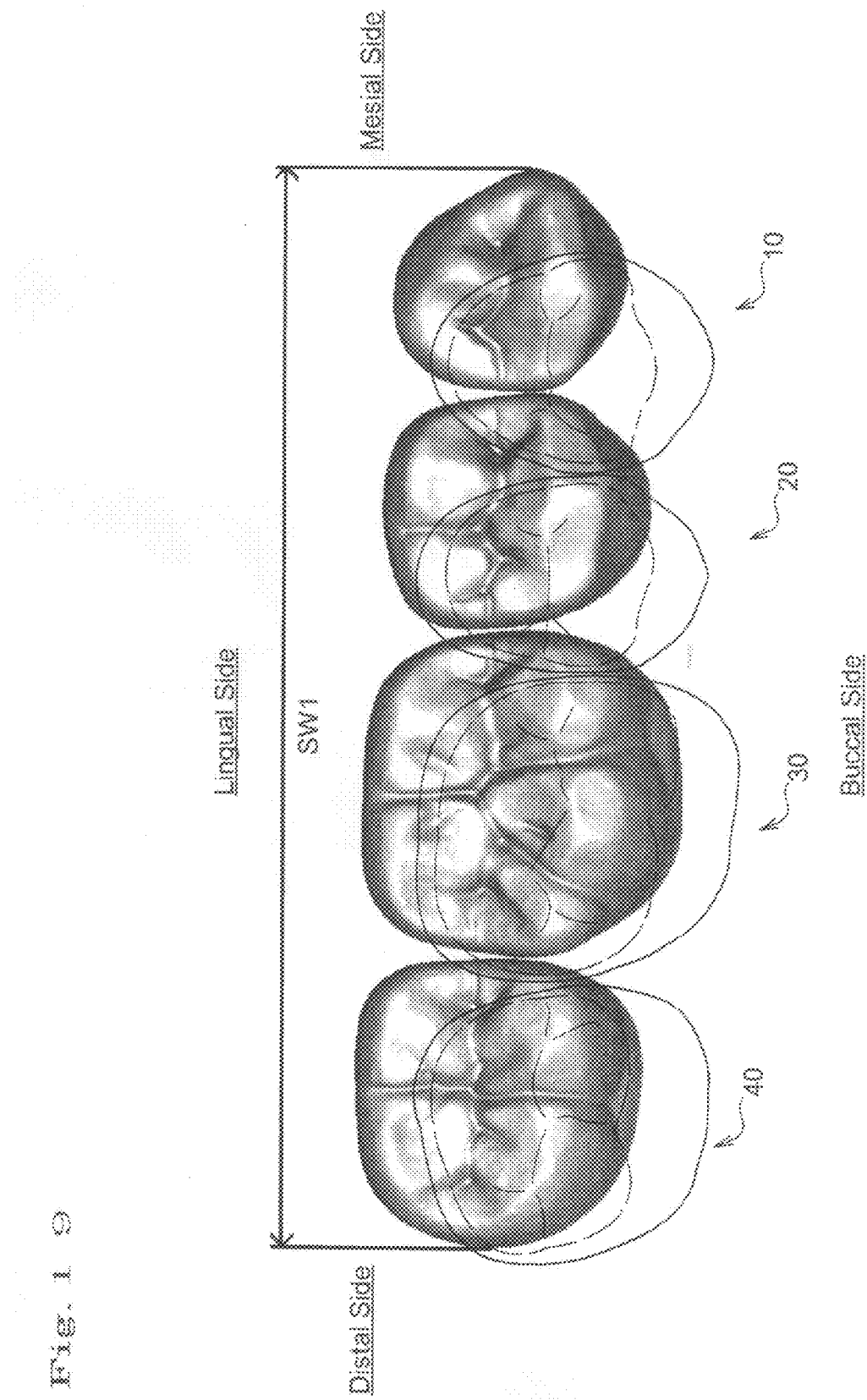

ARTIFICIAL TOOTH

TECHNICAL FIELD

The present invention relates to an artificial tooth preliminarily processed for use in manufacture of a plate denture.

BACKGROUND ART

An artificial tooth is a dental crown material preliminarily provided to a dentist or a dental technician in an anatomical form of a human tooth for use in manufacture of a plate denture. The artificial tooth is available in several types of shape, size and color, and is selected appropriately to be used depending on the condition of defect of the patient and the treatment plan.

A general fabricating method of a plate denture and a method of using the artificial tooth are briefly described below.

First, a model is fabricated by pouring plaster into a model of the oral shape of a patient which is taken by using an impression material such as silicone, agar or arginic acid.

The manufactured plaster model is installed in a device called an articulator having hinges similar to the temporomandibular joint of the patient. The artificial tooth selected according to the patient is positioned on the model while considering the entire balance and the occlusion of the upper and lower jaws. Then, the defect portion of peripheral tissues such as gum is formed by using paraffin wax so that a prototype of an entire denture called a wax denture is completed.

This denture with the model is embedded in plaster, the wax is removed to obtain a plaster model. In the plaster model, a denture based resin such as PMMA is injected, cured and hardened. The resin is taken out from the plaster model, polished and adjusted so that a denture is completed.

The plate denture is classified into a partial denture and a complete denture. The partial denture is a prosthetic appliance for compensating for the function and aesthetics of lost portion of dental root in oral in which natural teeth are partially remaining. The complete denture is a prosthetic appliance for covering the jaw losing all of the crown and root called an edentulous jaw.

A healthy person usually has 28 teeth or 32 teeth at maximum in oral. Since there exist combinations of processes of losing these teeth and various treatment plans by dentures, artificial teeth are used in a tremendous number of cases. Therefore, it has been demanded to satisfy various requirements by a limited number of types.

In particular, when occlusion of artificial teeth is required in upper and lower edentulous jaws, or dentulous jaws having similar degree of defects to the edentulous jaws, artificial teeth of upper and lower sets are used. At this time, for smooth operation, the artificial teeth are required to design the distribution of dimensions of tooth by booth so as to bite in a proper vertical direction preliminarily and to be positioned easily. However, actually such artificial teeth are rare, and the technician must decide the position while correcting the shape individually. Thus, it has been taking much time and labor to make the denture.

Patent document 1 discloses prosthetic posterior teeth formed to avoid mutual contact in lateral motion of mastication of buccal cusp. Patent document 2 discloses prosthetic posterior teeth in which the lower cusp of the maxillary posterior teeth bites and contacts with the fossa of the mandibular posterior teeth, and the buccal cusp of the mandibular posterior teeth bites and contacts with the fossa of the maxillary posterior teeth. Patent document 3 discloses prosthetic posterior teeth in which the buccal projection of the mandibular posterior teeth engages with the cleft of the maxillary posterior teeth, and the lingual projection of the maxillary posterior teeth engages with the longitudinal cleft of the mandibular posterior teeth.

In any of the patent documents, however, nothing is specified about the three-dimensional positional relation or contact region of all cusps and pits. Hence, even if artificial teeth of the mandibular posterior teeth are arranged without making gap, when attempted to position such that the artificial teeth of the mandibular posterior teeth bite the corresponding artificial teeth of the maxillary posterior teeth tooth by tooth, the artificial teeth of the adjacent maxillary posterior teeth may interfere with each other or a gap may be formed. Therefore, it was required to adjust and correct repeatedly.

Patent document 1: Japanese Patent Application Laid-Open No. 11-290347

Patent document 2: Japanese Patent Application Laid-Open No. 2002-177301

Patent document 3: Japanese Patent Publication No. 3747251

DISCLOSURE OF THE INVENTION

Problems to be Solved by the Invention

It is an object of the present invention to provide artificial teeth of easy operation of arrangement by clarifying the three-dimensional positional relation and contact region of the cusp tips and the fossa to be contacted with each other on occlusal surface in the maxillary and mandibular prosthetic posterior teeth pairing each other between the cusp tips and the fossa.

Means for Solving the Problems

The present invention relates to an artificial tooth of the mandibular first premolar tooth having a buccal cusp, a lingual cusp, a mesial pit, and a distal pit, in which the azimuth originating from the distal pit, the ratio of distance from the origin to the mesial surface, distal surface, buccal surface and lingual surface, and the positional relation between the cusp tip and the pit are appropriately set.

The present invention relates to an artificial tooth of the maxillary first premolar tooth having a buccal cusp, a lingual cusp, a mesial pit, and a distal pit, in which the azimuth originating from the lingual cusp tip, the ratio of distance from the origin to the mesial surface, distal surface, buccal surface and lingual surface, and the positional relation between the cusp tip and the pit are appropriately set.

Further, the present invention relates to a set of artificial teeth composed of the artificial tooth of the mandibular first premolar tooth and the artificial tooth of the maxillary first premolar tooth, in which the distal pit of the artificial tooth of the mandibular first premolar tooth and the lingual cusp tip of the artificial tooth of the maxillary first premolar tooth are made to contact with each other.

In this case, furthermore, the buccal cusp tip of the artificial tooth of the mandibular first premolar tooth and the mesial pit of the artificial tooth of the maxillary first premolar tooth are made to contact with each other.

The present invention relates to an artificial tooth of the mandibular second premolar tooth having a buccal cusp, a lingual cusp, a mesial pit, and a distal pit, in which the azimuth originating from the distal pit, the ratio of distance from the origin to the mesial surface, distal surface, buccal surface and lingual surface, and the positional relation between the cusp tip and the pit are appropriately set.

The present invention relates to an artificial tooth of the maxillary second premolar tooth having a buccal cusp, a lingual cusp, a mesial pit, and a distal pit, in which the azimuth originating from the lingual cusp tip, the ratio of distance from the origin to the mesial surface, distal surface, buccal surface and lingual surface, and the positional relation between the cusp tip and the pit are appropriately set.

Further, the present invention relates to a set of artificial teeth composed of the artificial tooth of the mandibular second premolar tooth and the artificial tooth of the maxillary second premolar tooth, in which the distal pit of the artificial tooth of the mandibular second premolar tooth and the lingual cusp tip of the artificial tooth of the maxillary second premolar tooth are made to contact with each other.

In this case, furthermore, the buccal cusp tip of the artificial tooth of the mandibular second premolar tooth and the mesial pit of the artificial tooth of the maxillary second premolar tooth are made to contact with each other.

The present invention relates to an artificial tooth of the mandibular first molar tooth having a mesial buccal cusp, a distal buccal cusp, a mesial lingual cusp, a distal lingual cusp, a distal cusp, a mesial pit, a distal pit, and a central pit, in which the azimuth originating from the central pit, the ratio of distance from the origin to the mesial surface, distal surface, buccal surface and lingual surface, and the positional relation between the cusp tip and the pit are appropriately set.

The present invention relates to an artificial tooth of the maxillary first molar tooth having a mesial buccal cusp, a distal buccal cusp, a mesial lingual cusp, a distal lingual cusp, a mesial pit, a distal pit, and a central pit, in which the azimuth originating from the mesial lingual cusp tip, the ratio of distance from the origin to the mesial surface, distal surface, buccal surface and lingual surface, and the positional relation between the cusp tip and the pit are appropriately set.

Further, the present invention relates to a set of artificial teeth composed of the artificial tooth of the mandibular first molar tooth and the artificial tooth of the maxillary first molar tooth, in which the central pit of the artificial tooth of the mandibular first molar tooth and the mesial lingual cusp tip of the artificial tooth of the maxillary first molar tooth are made to contact with each other.

In this case, furthermore, the mesial buccal cusp tip, distal buccal cusp tip, and distal pharyngeal cusp tip of the artificial tooth of the mandibular first molar tooth, and the mesial pit, central pit and distal pit of the artificial tooth of the maxillary first molar tooth are made to contact respectively with each other.

The present invention relates to an artificial tooth of the mandibular second molar tooth having a mesial buccal cusp, a distal buccal cusp, a mesial lingual cusp, a distal lingual cusp, a mesial pit, a distal pit, and a central pit, in which the azimuth originating from the central pit, the ratio of distance from the origin to the mesial surface, distal surface, buccal surface and lingual surface, and the positional relation between the cusp tip and the pit are appropriately set.

The present invention relates to an artificial tooth of the maxillary second molar tooth having a mesial buccal cusp, a distal buccal cusp, a mesial lingual cusp, a distal lingual cusp, a mesial pit, a distal pit, and a central pit, in which the azimuth originating from the mesial lingual cusp tip, the ratio of distance from the origin to the mesial surface, distal surface, buccal surface and lingual surface, and the positional relation between the cusp tip and the pit are appropriately set.

Further, the present invention relates to a set of artificial teeth composed of the artificial tooth of the mandibular second molar tooth and the artificial tooth of the maxillary second molar tooth, in which the central pit of the artificial tooth of the mandibular second molar tooth and the mesial lingual cusp tip of the artificial tooth of the maxillary second molar tooth are made to contact with each other.

In this case, furthermore, the mesial buccal cusp tip and distal buccal cusp tip of the artificial tooth of the mandibular second molar tooth, and the mesial pit and central pit of the artificial tooth of the maxillary second molar tooth are made to contact respectively with each other.

Furthermore, the present invention relates to a set of artificial teeth composed of an artificial tooth of the mandibular first premolar tooth, an artificial tooth of the mandibular second premolar tooth, an artificial tooth of the mandibular first molar tooth, and an artificial tooth of the mandibular second molar tooth, in which the maximum width of each artificial tooth is appropriately set.

Furthermore, the present invention relates to a set of artificial teeth consisting of an artificial tooth of the maxillary first premolar tooth, an artificial tooth of the maxillary second premolar tooth, an artificial tooth of the maxillary first molar tooth, and an artificial tooth of the maxillary second molar tooth, the maximum width of each artificial tooth is appropriately set.

Furthermore, the present invention relates to a set of artificial teeth composed of a set of artificial teeth of the mandibular molar teeth and a set of artificial teeth of the maxillary molar teeth, the sum of maximum widths of the set of artificial teeth of the maxillary molar teeth is appropriately set relative to the sum of maximum widths of the set of artificial teeth of the mandibular molar teeth.

Effects of the Invention

By using the artificial teeth of the present invention in manufacture of dentures, grinding adjustment during arrangement work is not needed, and therefore the dentures of a specific occlusion state can be manufactured efficiently in a short time.

Further, since the occlusion state is constant, the position required to adjust the occlusion after mounting the denture is limited to an early contact portion occurring due to error of curing strain and occlusion gain of the denture base resin, and the working time for occlusion adjustment is short, and the clinic hours can be shortened, and the labor of a dentist and the physical burden of a patient can be lessened.

BRIEF DESCRIPTION OF THE DRAWINGS

FIG. 17(a) shows an occlusal surface view showing the maximum width of each posterior tooth of a mandibular posterior dentition.
FIG. 17(b) shows an occlusal surface view showing the maximum width of each posterior tooth of a maxillary posterior dentition.
FIG. 18 is an occlusal surface view showing the sum of maximum widths of a maxillary posterior dentition and a mandibular posterior dentition.
FIG. 19 is an occlusal surface view showing the occlusion state of a maxillary posterior dentition and a mandibular posterior dentition.

DESCRIPTION OF THE REFERENCE NUMERALS

Figure 1:
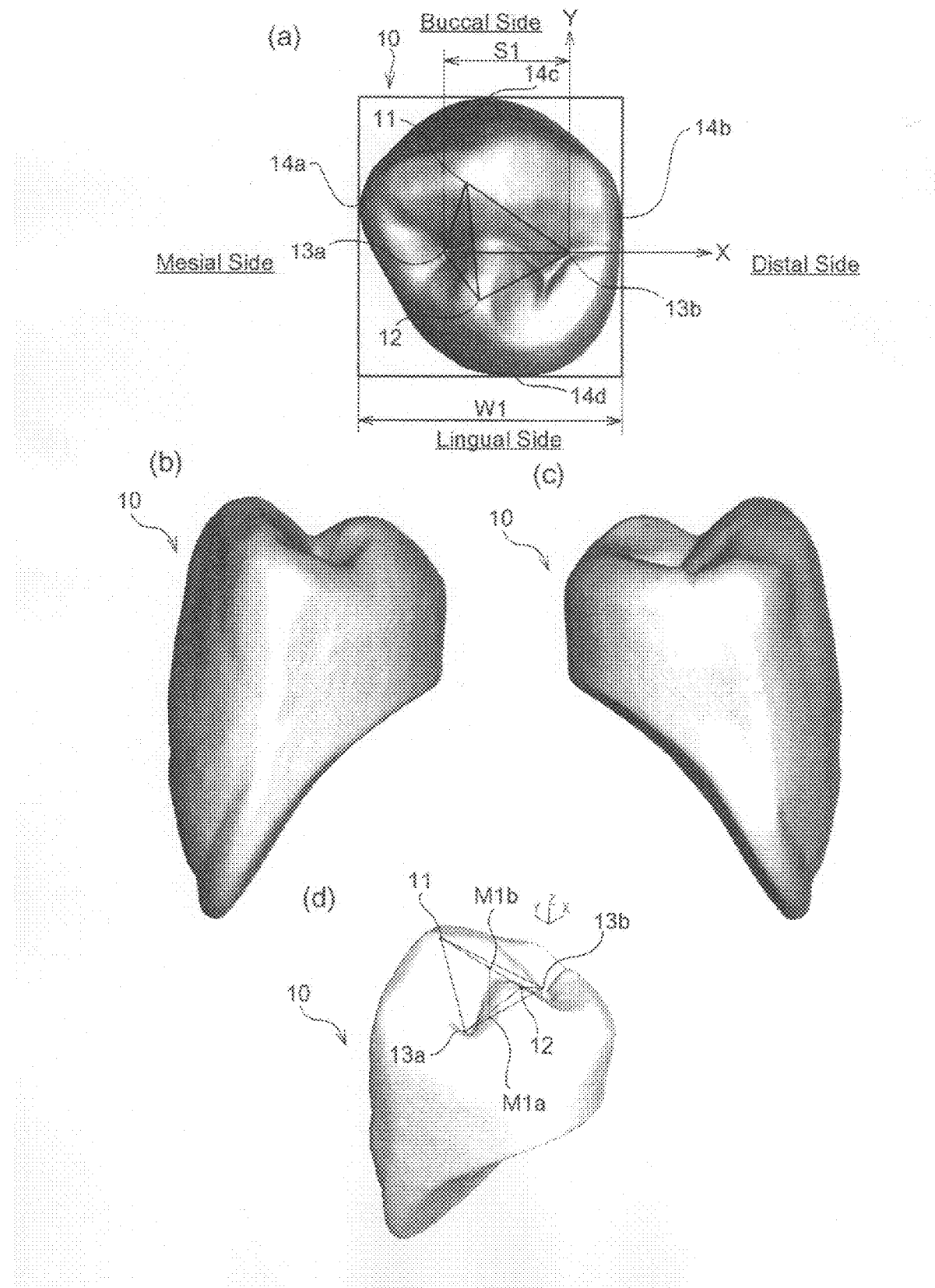
FIG. 1(a) shows an occlusal surface view of the mandibular first premolar tooth.
FIG. 1(b) shows a mesial surface view of the mandibular first premolar tooth.
FIG. 1(c) shows a distal surface view of the mandibular first premolar tooth.
FIG. 1(d) shows an oblique view of the mandibular first premolar tooth.

10 Mandibular first premolar tooth
11 Buccal cusp tip
12 Lingual cusp tip
13a Mesial pit
13b Distal pit
14a Minimum point of X-coordinate values on mesial surface
14b Maximum point of X-coordinate values on distal surface
14c Maximum point of Y-coordinate values on buccal surface
14d Minimum point of Y-coordinate values on lingual surface
20 Mandibular second premolar tooth
21 Buccal cusp tip
22 Lingual cusp tip
23a Mesial pit
23b Distal pit
24a Minimum point of X-coordinate values on mesial surface
24b Maximum point of X-coordinate values on distal surface
24c Maximum point of Y-coordinate values on buccal surface
24d Minimum point of Y-coordinate values on lingual surface
30 Mandibular first molar tooth
31a Mesial buccal cusp tip
31b Distal buccal cusp tip
31c Distal cusp tip
32a Mesial lingual cusp tip
32b Distal lingual cusp tip
33a Mesial pit
33b Distal pit
33c Central fossa
34a Minimum point of X-coordinate values on mesial surface
34b Maximum point of X-coordinate values on distal surface
34c Maximum point of Y-coordinate values on buccal surface
34d Minimum point of Y-coordinate values on lingual surface
40 Mandibular second molar tooth
41a Mesial buccal cusp tip
41b Distal buccal cusp tip
42a Mesial lingual cusp tip
42b Distal lingual cusp tip
43a Mesial pit
43b Distal pit
43c Central fossa
44a Minimum point of X-coordinate values on mesial surface
44b Maximum point of X-coordinate values on distal surface
44c Maximum point of Y-coordinate values on buccal surface
44d Minimum point of Y-coordinate values on lingual surface
50 Maxillary first premolar tooth
51 Buccal cusp tip
52 Lingual cusp tip
53a Mesial pit
53b Distal pit
54a Minimum point of X-coordinate values on mesial surface
54b Maximum point of X-coordinate values on distal surface
54c Maximum point of Y-coordinate values on buccal surface
54d Minimum point of Y-coordinate values on lingual surface
60 Maxillary second premolar tooth
61 Buccal cusp tip 62 Lingual cusp tip
63a Mesial pit
63b Distal pit
64a Minimum point of X-coordinate values on mesial surface
64b Maximum point of X-coordinate values on distal surface
64c Maximum point of Y-coordinate values on buccal surface
64d Minimum point of Y-coordinate values on lingual surface
70 Maxillary first molar tooth
71a Mesial buccal cusp tip
71b Distal buccal cusp tip
72a Mesial lingual cusp tip
72b Distal lingual cusp tip
73a Mesial pit
73b Distal pit
73c Central fossa
74a Minimum point of X-coordinate values on mesial surface
74b Maximum point of X-coordinate values on distal surface
74c Maximum point of Y-coordinate values on buccal surface
74d Minimum point of Y-coordinate values on lingual surface
80 Maxillary second molar tooth
81a Mesial buccal cusp tip
81b Distal buccal cusp tip
82a Mesial lingual cusp tip
82b Distal lingual cusp tip
83a Mesial pit
83b Distal pit
83c Central fossa
84a Minimum point of X-coordinate values on mesial surface
84b Maximum point of X-coordinate values on distal surface
84c Maximum point of Y-coordinate values on buccal surface
84d Minimum point of Y-coordinate values on lingual surface

BEST MODE FOR CARRYING OUT THE INVENTION

Before describing an embodiment of the present invention, names of anatomical features commonly used in both human posterior teeth and artificial posterior teeth are described.

Human posterior teeth are roughly divided into an upper section of teeth visible in appearance when a mouth is opened, and a lower section of teeth embedded in the alveolar bones. The upper section is called a dental crown, and the lower section is called a dental root. The dental crown is composed of five planes including relatively flat lateral surfaces in four directions.

With respect to the lateral directions, the side contacting with buccal mucosa is called a buccal side, and the side contacting with tongue is called a lingual side, and tooth surfaces are respectively called a buccal side surface and a lingual side surface. The side contacting with an adjacent tooth is called a proximal surface, and the side closer to the anterior tooth is called a mesial side, and the remoter side is called a distal side, and the respective tooth surfaces are called a mesial surface and a distal surface.

The surface biting with the paring tooth of the opposite side jaw is called an occlusal surface. The occlusal surface has complicated concave and convex portions, and the convex portions are called the cusps. Even in all posterior teeth, at least one cusp exists each at the buccal side and the lingual side, which are respectively called the buccal cusp and the lingual cusp. Furthermore, the molar tooth has its mesial and distal cusps, and the individual buccal cusps and the lingual cusps are called a mesial buccal cusp, a distal buccal cusp, a mesial lingual cusp, and a distal lingual cusp. The most projecting point of the cusp is called the cusp tip. In the description of the present invention, a provisional system of coordinates is set for clarifying the position, and in the system of coordinates, the cusp tip shows the maximum point of Z-coordinate values.

The occlusal surface is a range enclosed by four ridges, that is, a ridge extending from the buccal cusp tip to the mesial and distal sides, a ridge extending from the lingual cusp tip to the mesial and distal sides, a connecting portion of two ridges at the mesial side, and a connecting portion of two ridges at the distal side. These four ridges are called occlusal ridges, which are respectively called a buccal occlusal margin, a lingual occlusal margin, a mesial occlusal margin, and a distal occlusal margin. The particularly protruding portions of the mesial occlusal margin and distal occlusal margin are called marginal ridges, and called a mesial marginal ridge and a distal marginal ridge, respectively.

One cusp tip and the other cusp tip are separated by a deep groove, which is called a fissure. The fissure separating the buccal cusp tip and the lingual cusp tip is called a central fissure, the fissure separating the mesial buccal cusp tip and the distal buccal cusp tip on the molar tooth is called a buccal fissure, and the fissure separating the mesial lingual cusp tip and the distal lingual cusp tip is called a lingual fissure. The slope separated by the central fissure in the region enclosed by the occlusal margin of the occlusal surface is called an inner bevel, and the slope at the lingual side or buccal side from the occlusal margin is called an outer bevel.

The fissure separating the buccal cusp tip or the lingual cusp tip and the marginal ridge is called a triangular fissure. The triangular fissure exists in each one of the mesial buccal side, the distal buccal side, the mesial lingual side, and the distal lingual side.

A joining point of two or more fissures is deeply dented, which is called a pit.

The pit at joining point of the mesial buccal side triangular fissure, the mesial lingual side triangular fissure, and the central fissure is called a mesial pit.

The pit at joining point of the distal buccal side triangular fissure, the distal lingual side triangular fissure, and the central fissure is called a distal pit.

However, with respected to the distal pit of the lower side first molar tooth, a joining point of the distal buccal fissure is called a distal pit only in the mandibular first molar tooth in a description of page 154 of "Anatomy of permanent teeth of Japanese people" (published by Anatome). This pit is unclear, and it is hard to identify mostly in the existing artificial teeth. In all other teeth, the pit is defined at the joining point of the mesial and distal triangular fissures and the central fissure, and hence in the description of the present invention, according to the definition of the distal pit in other positions, the joining point of the distal triangular fissure and the central fissure is called the distal pit.

The joining point of the central fissure and the lingual fissure is called a central fossa.

The process running linearly from the cusp tip to the pit is called a triangular ridge.

A major axis of a tooth is called a dental axis. The dental axis is a line segment connecting from the central part of the dental crown to the central part of the dental root. Since it is difficult to identify the center of a non-symmetrical tooth, in the description of the present invention, it is expressed by the line segment connecting between a point for dividing the line segment connecting between the mesial pit and a distal pit at a specific ratio in each position, and the point for dividing the line segment connecting between the distal buccal cusp tip and the mesial lingual cusp tip at a specific ratio in each position.

Dimensions of a tooth profile are generally expressed by the width diameter, the major diameter, and the buccal lingual diameter.

To measure the dimensions of a tooth profile, it is desired to determine in the condition of fixing the tooth at a specific position. A specific measuring method is described below.

First, a system of XYZ three-dimensional coordinates in which the lateral direction on a horizontal plane is the X-axis, the direction from the near side to the inner side is the Y-axis, and the direction of height is the Z-axis is set. A measuring table is prepared, which is capable of measuring the distance between planes when the object is enclosed by planes orthogonal in each axial direction of the system of coordinate. It is preferred to use a contact type or non-contact type three-dimensional measuring instrument, but in a simple method, three micro gauges or vernier calipers capable of measuring in the unit of 0.01 mm are prepared, and installed orthogonally on a desk or other horizontal plane.

The instruments are provisionally adhered to the base of the artificial tooth to be measure by using soft wax for fine adjustment of position, and fixed firmly by using an adhesive or the like after adjustment.

The fixing position is determined, setting the occlusal surface as the upside, by the X-axis in mesial-distal direction, the Y-axis in buccal-lingual direction, and the Z-axis in height direction. At this time, the mesial pit and the distal pit are parallel to the XZ plane, that is, the position is finely adjusted so that the Y-coordinate values at the pit positions are equal, and that the dental axis of the tooth may be parallel to the Z-axis. The dental axis in the description of the present invention, as mentioned above, the line segment connecting between the point for dividing the line segment connecting between the mesial pit and the distal pit at a specific ratio in each position, and the point for dividing the line segment connecting between the distal buccal cusp tip and the mesial lingual cusp tip at a specific ratio in each position.

A set of artificial teeth is provided in a combination of artificial teeth of all positions of upper and lower jaws, which are dimensionally expressed by one common count.

Next, an embodiment of each of the artificial teeth of the present invention is described below.

The numerical values mentioned below are in a range based on the dimensional precisions all actually can be provided. A more preferable range is a range based on the dimensional precision capable of judging the effects of the present invention visually.

In the following embodiments, the right side posterior teeth are described, but the left side posterior teeth are made uniform in operability, and it is desired to be in mirror symmetrical relation with the right side. Specifically, it is possible to manufacture by a mold processing method using a shape model inverted in the mesial-distal direction by a CAD system, or a mold processing method by mirror inverting method of the mold processing data itself.

<Artificial Tooth of Mandibular First Premolar Tooth>

FIG. 1 shows an artificial tooth of a mandibular first premolar tooth 10. In the figure, the left side is the mesial side, the right side is the distal side, the upside is the buccal side, and the downside is the lingual side.

The artificial tooth of the mandibular first premolar tooth 10 has a buccal cusp tip 11, a lingual cusp tip 12, a mesial pit 13a, and a distal pit 13b.

In order to clarify the three-dimensional positional relation of the cusp tips and the pits, in an example of the right side, when supposing the distal pit 13b to be the origin of the virtual system of XYZ orthogonal coordinates of this tooth, as shown in FIG. 1, the dental axis is the line segment connecting between point M1a for dividing the line segment connecting between the mesial pit 13a and the distal pit 13b by 29:71 and point M1b for dividing the line segment connecting between the buccal cusp tip 11 and the lingual cusp tip 12 by 47:53, and an arrangement is determined such that it is parallel to the Z-axis, that the line segment connecting between the mesial pit 13a and the distal pit 13b may be parallel to the XZ plane of the system of XYZ orthogonal coordinates, and that the condition is satisfied in the relation of X-coordinate value of mesial pit 13a<X-coordinate value of distal pit 13b.

The mesial surface, the distal surface, the buccal surface and the lower surface of the mandibular first premolar tooth 10 are defined in the following relation.

The ratio of the distance of X-axis from the distal pit 13b to minimum position 14a of X-coordinate value of the mesial surface of the tooth, and the distance of X-axis from the distal pit 13b to maximum position 14b of X-coordinate value of the distal surface of the tooth is 75:25 to 85:15, and preferably 78:22 to 82:18.

The ratio of the distance of Y-axis from the distal pit 13b to maximum position 14c of Y-coordinate value of the buccal surface of the tooth, and the distance of Y-axis from the distal pit 13b to maximum position 14d of Y-coordinate value of the lingual surface of the tooth is 49:51 to 59:41, and preferably 52:49 to 56:44.

Each of the cusp tips and each of the pits of the mandibular first premolar tooth 10 are defined in the following relation. Here, the distance of line segment connecting between the mesial pit 13a and the distal pit 13b is set as S1, and the maximum width of the mandibular first premolar tooth 10 is set as W1.

The distance S1 of the line segment connecting between the mesial pit 13a and the distal pit 13b is 42 to 52% of the maximum width W1, and preferably 46 to 48%.

The distance of the line segment connecting between the mesial pit 13a and the buccal cusp tip 11 is 84 to 94% of the distance S1 of the line segment connecting between the mesial pit 13a and the distal pit 13b, and preferably 88 to 90%.

The distance of the line segment connecting between the mesial pit 13a and the lingual cusp tip 12 is 66 to 76% of the distance S1 of the line segment connecting between the mesial pit 13a and the distal pit 13b, and preferably 70 to 72%.

The distance of the line segment connecting between the distal pit 13b and the buccal cusp tip 11 is 110 to 120% of the distance S1 of the line segment connecting between the mesial pit 13a and the distal pit 13b, and preferably 114 to 116%.

The distance of the line segment connecting between the distal pit 13b and the lingual cusp tip 12 is 83 to 93% of the distance S1 of the line segment connecting between the mesial pit 13a and the distal pit 13b, and preferably 87 to 89%.

The distance of the line segment connecting between the buccal cusp tip 11 and the lingual cusp tip 12 is 88 to 98% of the distance S1 of the line segment connecting between the mesial pit 13a and the distal pit 13b, and preferably 92 to 94%.

<Artificial Tooth of Maxillary First Premolar Tooth>

Figure 2:
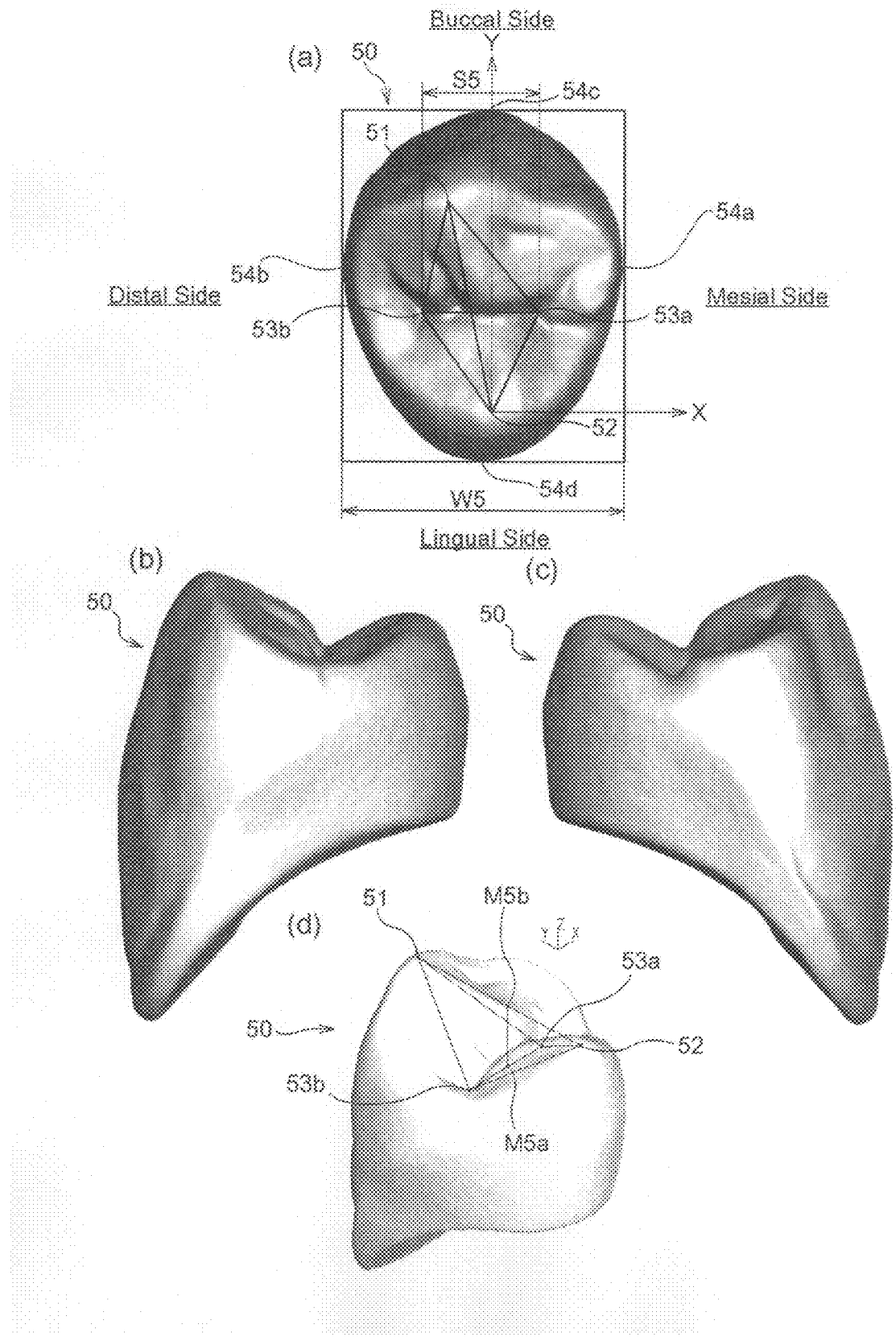
FIG. 2(a) shows an occlusal surface view of the maxillary first premolar tooth.
FIG. 2(b) shows a mesial surface view of the maxillary first premolar tooth.
FIG. 2(c) shows a distal surface view of the maxillary first premolar tooth.
FIG. 2(d) shows an oblique view of the maxillary first premolar tooth.

FIG. 2 shows an artificial tooth of a maxillary first premolar tooth 50. In the figure, the left side is the distal side, the right side is the mesial side, the upside is the buccal side, and the downside is the lingual side.

The artificial tooth of the maxillary first premolar tooth 50 has a buccal cusp tip 51, a lingual cusp tip 52, a mesial pit 53a, and a distal pit 53b.

In order to clarify the three-dimensional positional relation of the cusp tips and the pits, in an example of the right side, when supposing the lingual cusp tip 52 to be the origin of the virtual system of XYZ orthogonal coordinates of this tooth, an arrangement is determined such that the line segment connecting between point M5a for dividing the line segment connecting between the mesial pit 53a and the distal pit 53b by 47:53 and point M5b for dividing the line segment connecting between the buccal cusp tip 51 and the lingual cusp tip 52 by 55:45 is parallel to the Z-axis, that the segment connecting between the mesial pit 53a and the distal pit 53b is parallel to the XZ plane of the system of XYZ orthogonal coordinates, and that the condition is satisfied in the relation of X-coordinate value of mesial pit 52a>X-coordinate value of distal pit 53b.

The mesial surface, the distal surface, the buccal surface and the lower surface of the maxillary first premolar tooth 50 are defined in the following relation.

The ratio of the distance of X-axis from the lingual cusp tip 52 to maximum position 54a of X-coordinate value of the mesial surface of the tooth, and the distance of X-axis from the lingual cusp tip 52 to minimum position 54b of X-coordinate value of the distal surface of the tooth is 37:63 to 47:53, and preferably 41:59 to 43:57.

The ratio of the distance of Y-axis from the lingual cusp tip 52 to maximum position 54c of Y-coordinate value of the lingual surface of the tooth, and the distance of Y-axis from the lingual cusp tip 52 to minimum position 54d of Y-coordinate value of the buccal surface of the tooth is 79:21 to 89:11, and preferably 83:17 to 85:15.

Each of the cusp tips and each of the pits of the maxillary first premolar tooth 50 are defined in the following relation. Here, the distance of line segment connecting between the mesial pit 53a and the distal pit 53b is set as S5, and the maximum width of the maxillary first premolar tooth 50 is set as W5.

The distance S5 of the line segment connecting between the mesial pit 53a and the distal pit 53b is 36 to 46% of the maximum width W5, and preferably 40 to 42%.

The distance of the line segment connecting between the mesial pit 53a and the buccal cusp tip 51 is 147 to 157% of the distance S5 of the line segment connecting between the mesial pit 53a and the distal pit 53b, and preferably 151 to 153%.

The distance of the line segment connecting between the mesial pit 53a and the lingual cusp tip 52 is 98 to 108% of the distance S5 of the line segment connecting between the mesial pit 53a and the distal pit 53b, and preferably 102 to 104%.

The distance of the line segment connecting between the distal pit 53b and the buccal cusp tip 51 is 134 to 144% of the distance S5 of the line segment connecting between the mesial pit 53a and the distal pit 53b, and preferably 138 to 140%.

The distance of the line segment connecting between the distal pit 53b and the lingual cusp tip 52 is 119 to 129% of the distance S5 of the line segment connecting between the mesial pit 53a and the distal pit 53b, and preferably 123 to 125%.

The distance of the line segment connecting between the buccal cusp tip 51 and the lingual cusp tip 52 is 185 to 195% of the distance S5 of the line segment connecting between the mesial pit 53a and the distal pit 53b, and preferably 189 to 191%.

<A Set of Artificial Teeth of Mandibular First Premolar Tooth and Maxillary First Premolar Tooth>

Figure 3:
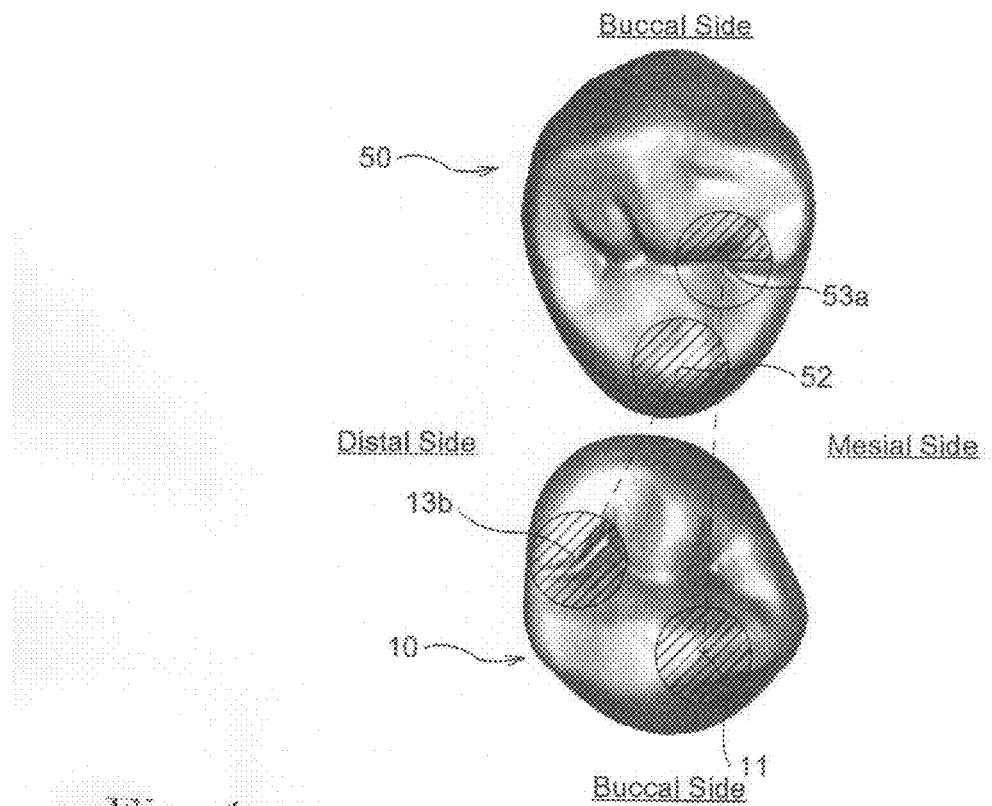
FIG. 3 shows an occlusal surface view of the mandibular first premolar tooth and the maxillary first premolar tooth.
Figure 4:
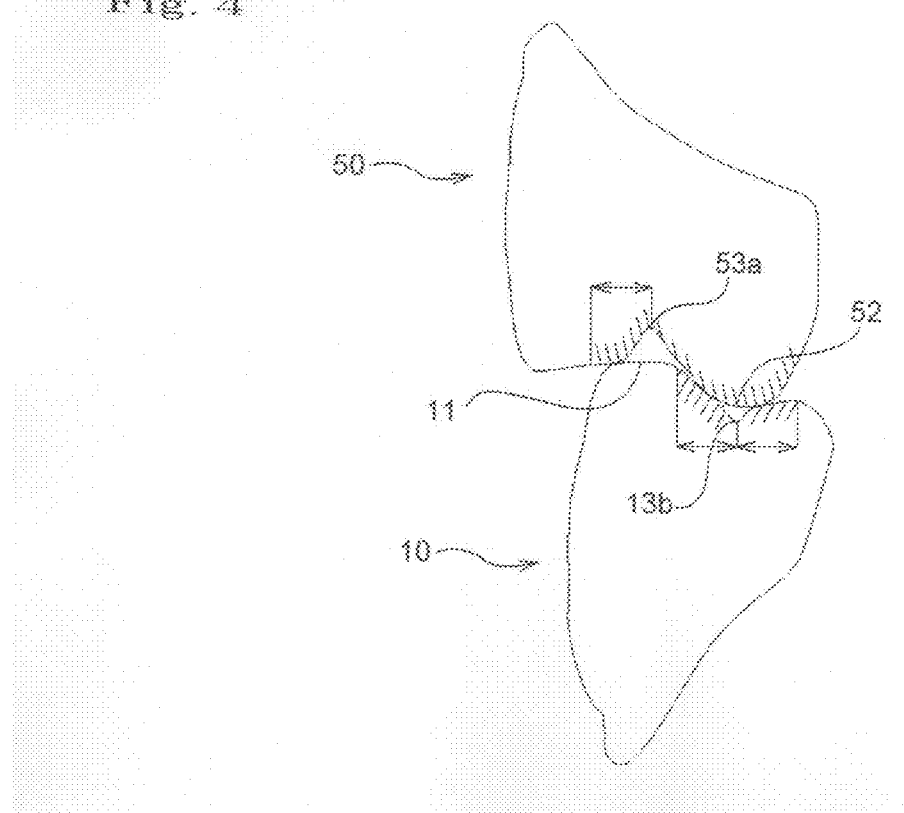
FIG. 4 shows a contact state sectional view of the mandibular first premolar tooth and the maxillary first premolar tooth.

FIG. 3 and FIG. 4 show the set of artificial teeth of the mandibular first premolar tooth 10 and the maxillary first premolar tooth 50. In the occlusal surface within 1.50 mm in radius from the distal pit 13b of the artificial tooth of the mandibular first premolar tooth 10, there is at least one contact point with the occlusal surface within 1.50 mm in radius from the lingual cusp tip 52 of the artificial tooth of the maxillary first premolar tooth 50.

Preferably, there are three contact points in total, that is, one contact point between the buccal cusp inner bevel within 1.00 mm from the distal pit 13b of the mandibular first premolar tooth 10 and the lingual cusp inner bevel within 1.00 mm from the lingual cusp tip 52 of the maxillary first premolar tooth 50, one contact point between the distal marginal ridge within 1.00 mm from the distal pit 13b of the mandibular first premolar tooth 10 and the outer bevel from the distal occlusal margin within 1.00 mm from the lingual cusp tip 52 of the maxillary first premolar tooth 50, and one contact point between the lingual cusp inner bevel within 1.00 mm from the distal pit 13b of the mandibular first premolar tooth 10 and the outer bevel from the mesial occlusal margin within 1.00 mm from the lingual cusp tip 52 of the maxillary first premolar tooth 50.

Accordingly, contact points are formed in a small region of the occlusal surface, and therefore it is easy to check the occlusal state, and effects of efficient arrangement can be expected.

Furthermore, the set of artificial teeth of the mandibular first premolar tooth 10 and the maxillary first premolar tooth 50 has at least one contact point between the occlusal surface within 1.50 mm from the buccal cusp tip 11 of the artificial tooth of the mandibular first premolar tooth 10 and the occlusal surface within 1.50 mm from the mesial pit 53a of the maxillary first premolar tooth 50.

Preferably, there are two contact points in total, that is, one contact point between the mesial occlusal margin within 1.00 mm from the buccal cusp tip 11 of the mandibular first premolar tooth 10 and the mesial marginal ridge within 1.00 mm from the mesial pit 53a of the maxillary first premolar tooth 50, and one contact point between the distal occlusal margin within 1.00 mm from the buccal cusp tip 11 of the mandibular first premolar tooth 10 and the triangular ridge on the buccal inner bevel within 1.00 mm from the mesial pit 53a of the maxillary first premolar tooth 50.

Accordingly, contact points are formed in a small region of the occlusal surface, and therefore it is easy to check the occlusal state, and effects of efficient arrangement can be expected.

<Artificial Tooth of Mandibular Second Premolar Tooth>

Figure 5:
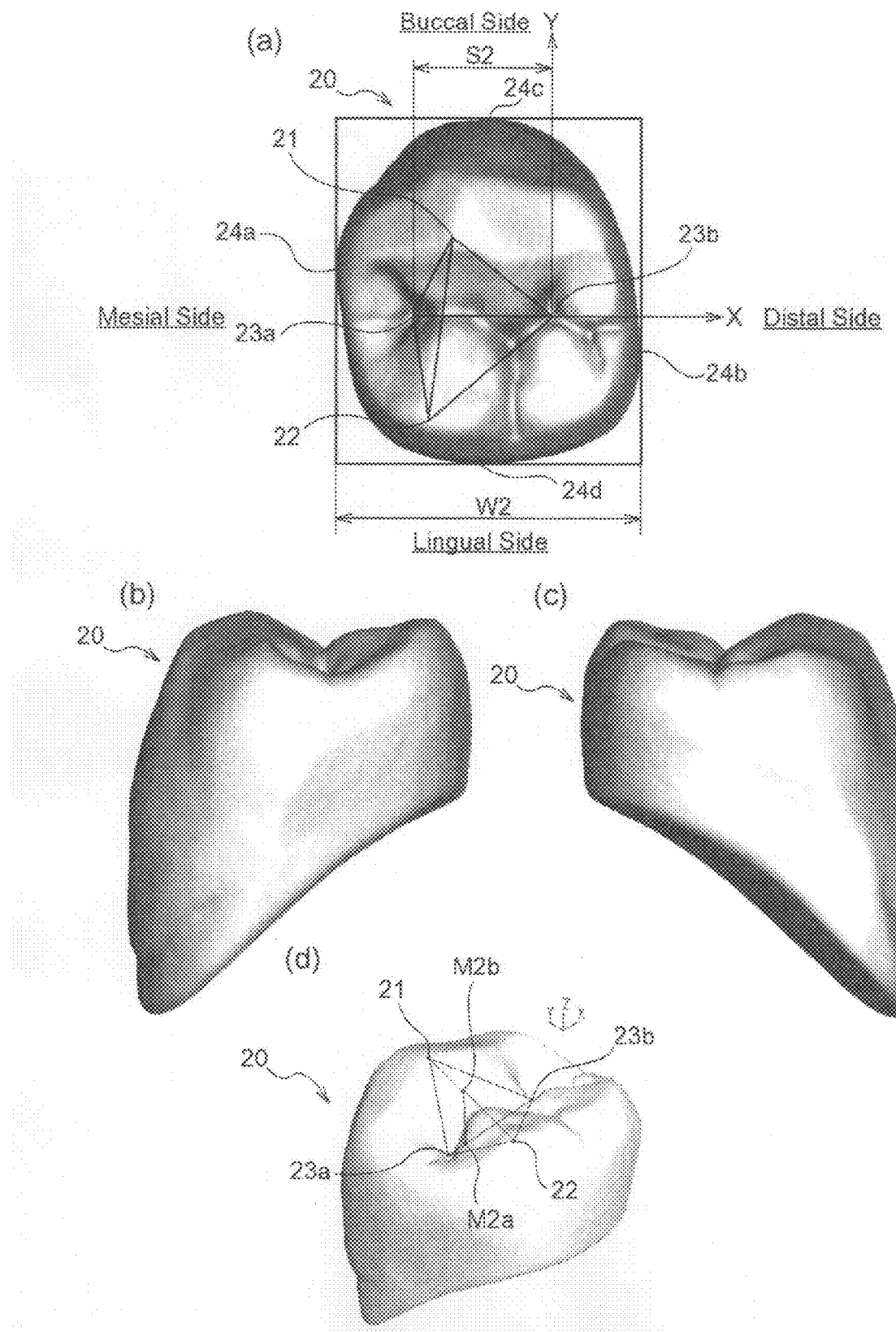
FIG. 5(a) shows an occlusal surface view of the mandibular second premolar tooth.
FIG. 5(b) shows a mesial surface view of the mandibular second premolar tooth.
FIG. 5(c) shows a distal surface view of the mandibular second premolar tooth.
FIG. 5(d) shows an oblique view of the mandibular second premolar tooth.

FIG. 5 shows an artificial tooth of a mandibular second premolar tooth 20. In the figure, the left side is the mesial side, the right side is the distal side, the upside is the buccal side, and the downside is the lingual side.

The artificial tooth of the mandibular second premolar tooth 20 has a buccal cusp tip 21, a lingual cusp tip 22, a mesial pit 23a, and a distal pit 23b.

In order to clarify the three-dimensional positional relation of the cusp tips and the pits, in an example of the right side, when supposing the distal pit 23b to be the origin of the virtual system of XYZ orthogonal coordinates of this tooth, an arrangement is determined such that the line segment connecting between a point M2a for dividing the line segment connecting between the mesial pit 23a and the distal pit 23b by 21:79 and a point M2b for dividing the line segment connecting between the buccal cusp tip 21 and the lingual cusp tip 22 by 40:60 is parallel to the Z-axis, that the line segment connecting between the mesial pit 23a and the distal pit 23b is parallel to the XZ plane of the XZ plane of the system of XYZ orthogonal coordinates, and that the condition is determined in the relation of X-coordinate value of mesial pit<X-coordinate value of distal pit.

The mesial surface, the distal surface, the buccal surface and the lower surface of the mandibular second premolar tooth 20 are defined in the following relation.

The ratio of the distance of X-axis from the distal pit 23b to minimum position 24a of X-coordinate value of the mesial surface of the tooth, and the distance of X-axis from the distal pit 23b to maximum position 24b of X-coordinate value of the distal surface of the tooth is 66:34 to 76:24, and preferably 70:20 to 72:28.

The ratio of the distance of Y-axis from the distal pit 23b to maximum position 24c of Y-coordinate value of the buccal surface of the tooth, and the distance of Y-axis from the distal pit 23b to minimum position 24d of Y-coordinate value of the lingual surface of the tooth is 51:49 to 61:39, and preferably 55:45 to 57:43.

Each of the cusp tips and each of the pits of the mandibular second premolar tooth 20 are defined in the following relation. Here, the distance of line segment connecting between the mesial pit 23a and the distal pit 23b is set as S2, and the maximum width of the mandibular second premolar tooth 20 is set as W2.

The distance S2 of the line segment connecting between the mesial pit 23a and the distal pit 23b is 56 to 66% of the maximum width W2, and preferably 60 to 62%.

The distance of the line segment connecting between the mesial pit 23a and the buccal cusp tip 21 is 79 to 89% of the distance S2 of the line segment connecting between the mesial pit 23a and the distal pit 23b, and preferably 83 to 85%.

The distance of the line segment connecting between the mesial pit 23a and the lingual cusp tip 22 is 88 to 98% of the distance S2 of the line segment connecting between the mesial pit 23a and the distal pit 23b, and preferably 92 to 94%.

The distance of the line segment connecting between the distal pit 23b and the buccal cusp tip 21 is 97 to 107% of the distance S2 of the line segment connecting between the mesial pit 23a and the distal pit 23b, and preferably 101 to 103%.

The distance of the line segment connecting between the distal pit 23b and the lingual cusp tip 22 is 127 to 137% of the distance S2 of the line segment connecting between the mesial pit 23a and the distal pit 23b, and preferably 131 to 133%.

The distance of the line segment connecting between the buccal cusp tip 21 and the lingual cusp tip 22 is 126 to 136% of the distance S2 of the line segment connecting between the mesial pit 23a and the distal pit 23b, and preferably 130 to 132%.

<Artificial Tooth of Maxillary Second Premolar Tooth>

Figure 6:
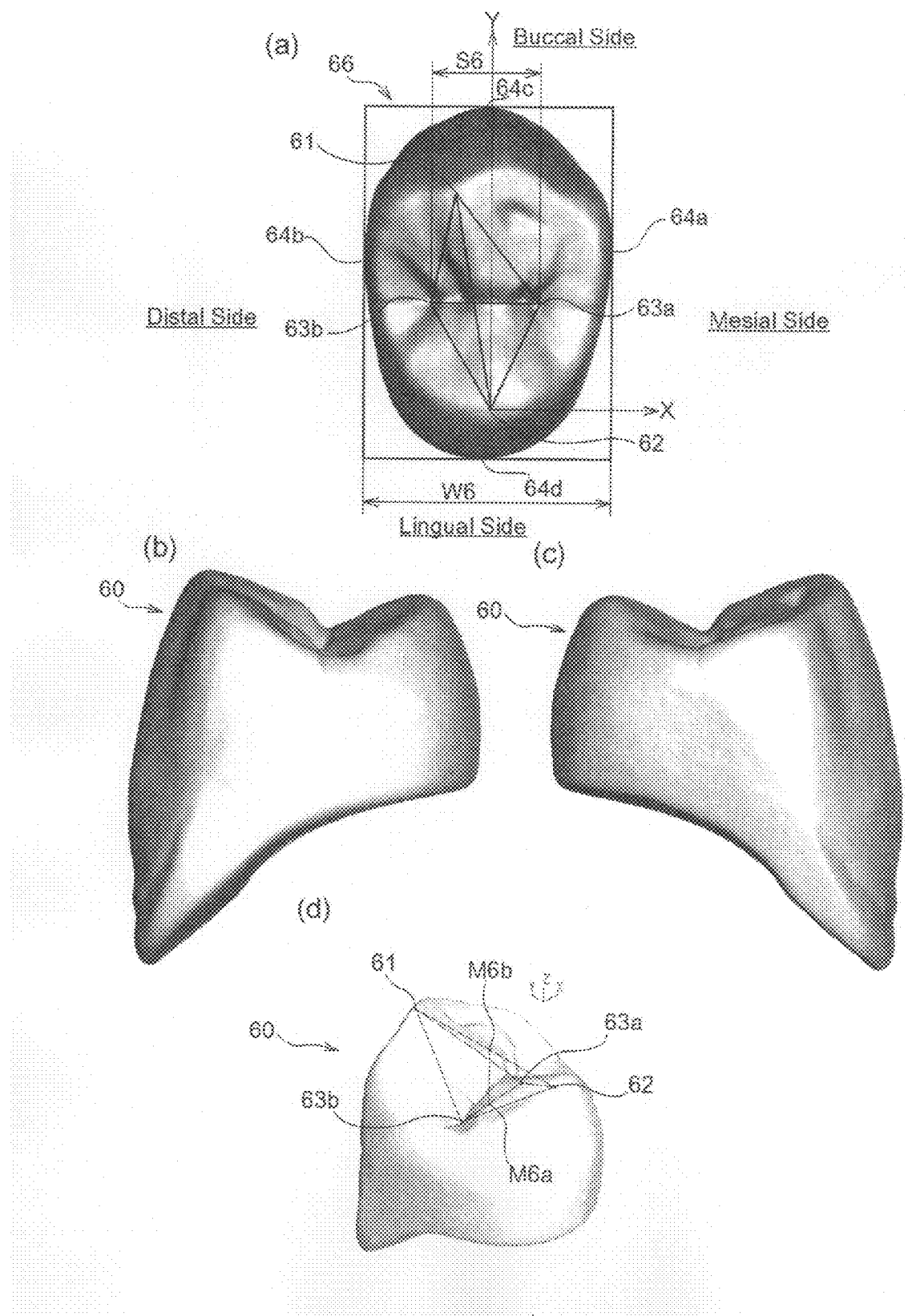
FIG. 6(a) shows an occlusal surface view of the maxillary second premolar tooth.
FIG. 6(b) shows a mesial surface view of the maxillary second premolar tooth.
FIG. 6(c) shows a distal surface view of the maxillary second premolar tooth.
FIG. 6(d) shows an oblique view of the maxillary second premolar tooth.

FIG. 6 shows an artificial tooth of a maxillary second premolar tooth 60. In the figure, the left side is the distal side, the right side is the mesial side, the upside is the buccal side, and the downside is the lingual side.

The artificial tooth of the maxillary second premolar tooth 60 has a buccal cusp tip 61, a lingual cusp tip 62, a mesial pit 63a, and a distal pit 63b.

In order to clarify the three-dimensional positional relation of the cusp tips and the pits, in an example of the right side, when supposing the lingual cusp tip 62 to be the origin of the virtual system of XYZ orthogonal coordinates of this tooth, an arrangement is determined such that the line segment connecting between a point M6a for dividing the line segment connecting between the mesial pit 63a and the distal pit 63b by 54:46 and a point M6b for dividing the line segment connecting between the buccal cusp tip 61 and the lingual cusp tip 62 by 53:47 is parallel to the Z-axis of the system of XYZ orthogonal coordinates, that the segment connecting between the distal pit 63b and the mesial pit 63a is parallel to the XZ plane of the system of XYZ orthogonal coordinates, and that the condition is satisfied in the relation of X-coordinate value of mesial pit 63a>X-coordinate value of distal pit.

The mesial surface, the distal surface, the buccal surface and the lower surface of the maxillary second premolar tooth 60 are defined in the following relation.

The ratio of the distance of X-axis from the lingual cusp tip 62 to maximum position 64a of X-coordinate value of the mesial surface of the tooth, and the distance of X-axis from the lingual cusp tip 62 to minimum position 64b of X-coordinate value of the distal surface of the tooth is 42:68 to 52:58, and preferably 46:54 to 48:52.

The ratio of the distance of Y-axis from the lingual cusp tip 62 to maximum position 64c of Y-coordinate value of the buccal surface of the tooth, and the distance of Y-axis from the lingual cusp tip 62 to minimum position 64d of Y-coordinate value of the lingual surface of the tooth is 79:21 to 89:11, and preferably 83:17 to 85:15.

Each of the cusp tips and each of the pits of the maxillary second premolar tooth 60 are defined in the following relation. The distance of line segment connecting between the mesial pit 63a and the distal pit 63b is set as S6, and the maximum width of the maxillary second premolar tooth 60 is set as W6.

The distance S6 of the line segment connecting between the mesial pit 63a and the distal pit 63b is 40 to 50% of the maximum width W6, and preferably 44 to 46%.

The distance of the line segment connecting between the mesial pit 63a and the buccal cusp tip 61 is 150 to 160% of the distance S6 of the line segment connecting between the mesial pit 63a and the distal pit 63b, and preferably 154 to 156%.

The distance of the line segment connecting between the mesial pit 63a and the lingual cusp tip 62 is 117 to 127% of the distance S6 of the line segment connecting between the mesial pit 63a and the distal pit 63b, and preferably 121 to 123%.

The distance of the line segment connecting between the distal pit 63b and the buccal cusp tip 61 is 142 to 132% of the distance S6 of the line segment connecting between the mesial pit 63a and the distal pit 63b, and preferably 146 to 148%.

The distance of the line segment connecting between the distal pit 63b and the lingual cusp tip 62 is 128 to 138% of the distance S6 of the line segment connecting between the mesial pit 63a and the distal pit 63b, and preferably 132 to 134%.

The distance of the line segment connecting between the buccal cusp tip 61 and the lingual cusp tip 62 is 204 to 214% of the distance S6 of the line segment connecting between the mesial pit 63a and the distal pit 63b, and preferably 208 to 210%.

<A Set of Artificial Teeth of Mandibular Second Premolar Tooth and Maxillary Second Premolar Tooth>

Figure 7:
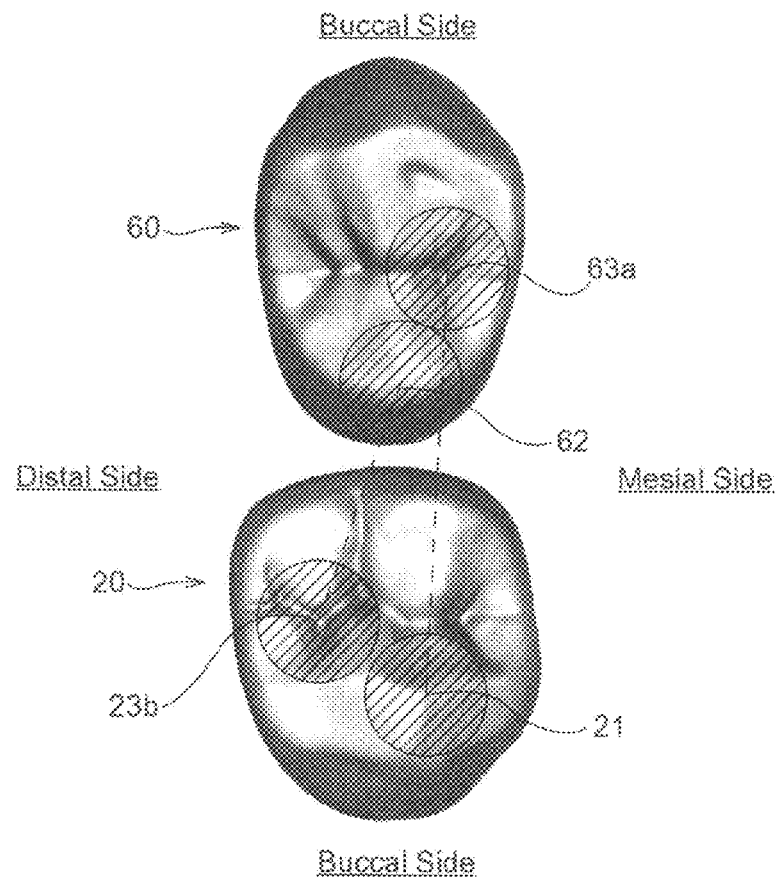
FIG. 7 shows an occlusal surface view of the mandibular second premolar tooth and the maxillary second premolar tooth.
Figure 8:
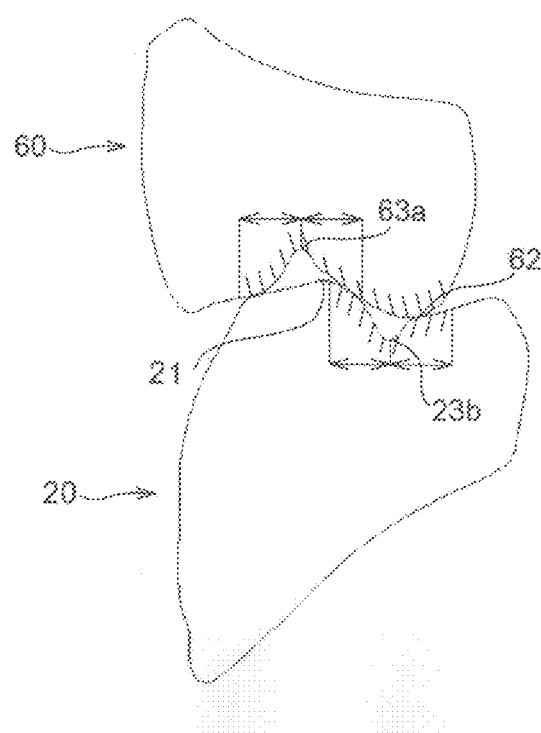
FIG. 8 shows a contact state sectional view of the mandibular second premolar tooth and the maxillary second premolar tooth.

FIG. 7 and FIG. 8 show the set of artificial teeth of the mandibular second premolar tooth 20 and the maxillary second premolar tooth 60.

With respect to the set of artificial teeth of the maxillary second premolar tooth 60 and the mandibular second premolar tooth 20, in the occlusal surface within 1.50 mm in radius from the distal pit 23b of the artificial tooth of the mandibular second premolar tooth 20, there is at least one contact point with the occlusal surface within 1.50 mm in radius from the lingual cusp tip 62 of the artificial tooth of the maxillary second premolar tooth 60.

Preferably, there are three contact points in total, that is, one contact point between the buccal cusp inner bevel within 1.00 mm from the distal pit 23b of the mandibular second premolar tooth 20 and the lingual cusp inner bevel within 1.00 mm from the lingual cusp tip 62 of the maxillary second premolar tooth 60, one contact point between the distal marginal ridge within 1.00 mm from the distal pit 23b of the mandibular second premolar tooth 20 and the outer bevel from the distal occlusal margin within 1.00 mm from the lingual cusp tip 62 of the maxillary second premolar tooth 60, and one contact point between the lingual cusp inner bevel within 1.00 mm from the distal pit 23b of the mandibular second premolar tooth 20 and the outer bevel from the mesial occlusal margin within 1.00 mm from the lingual cusp tip 62 of the maxillary first premolar tooth 60.

Accordingly, contact points are formed in a small region of the occlusal surface, and therefore it is easy to check the occlusal state, and effects of efficient arrangement can be expected.

Furthermore, the set of artificial teeth of the mandibular second premolar tooth 20 and the maxillary second premolar tooth 60 has at least one contact point with the occlusal surface within 1.50 mm in radius from the mesial pit 63a of the artificial tooth of the maxillary second premolar tooth 60 on the occlusal surface within 1.50 mm in radius from the buccal cusp tip 21 of the artificial tooth of the mandibular second premolar tooth 20.

Preferably, there are two contact points in total, that is, one contact point between the mesial occlusal margin within 1.00 mm from the buccal cusp tip 21 of the artificial tooth of the mandibular second premolar tooth 20 and the mesial marginal ridge within 1.00 mm from the mesial pit 63a of the artificial tooth of the maxillary second premolar tooth 60, and one contact point between the distal occlusal margin within 1.00 mm from the buccal cusp tip 21 of the mandibular second premolar tooth 20 and the triangular ridge on the buccal inner bevel within 1.00 mm from the mesial pit 63a of the maxillary first premolar tooth 60.

Accordingly, contact points are formed in a small region of the occlusal surface, and therefore it is easy to check the occlusal state, and effects of efficient arrangement can be expected.

<Artificial Tooth of Mandibular First Molar Tooth>

Figure 9:
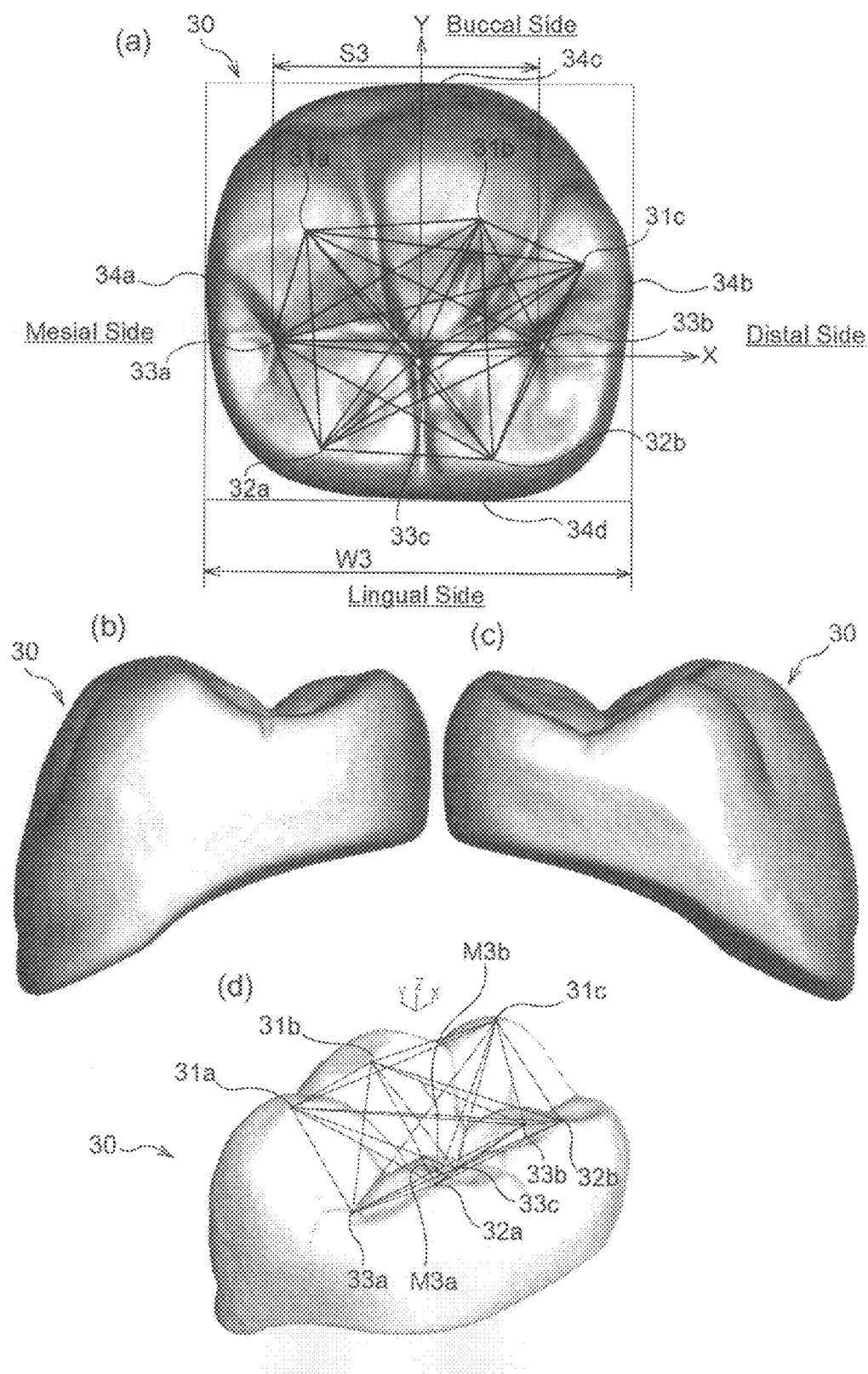
FIG. 9(a) shows an occlusal surface view of the mandibular first molar tooth.
FIG. 9(b) shows a mesial surface view of the mandibular first molar tooth.
FIG. 9(c) shows a distal surface view of the mandibular first molar tooth.
FIG. 9(d) shows an oblique view of the mandibular first molar tooth.

FIG. 9 shows an artificial tooth of a mandibular first molar tooth 30. In the figure, the left side is the mesial side, the right side is the distal side, the upside is the buccal side, and the downside is the lingual side.

The artificial tooth of the mandibular first molar tooth 30 has a mesial buccal cusp tip 31a, distal buccal cusp tip 31b, a mesial lingual cusp tip 32a, a distal lingual cusp tip 32b, a mesial pit 33a, a distal pit 33b, and a central fossa 33c.

In order to clarify the three-dimensional positional relation of the cusp tips and the pits, in an example of the right side, when supposing the central fossa 33c to be the origin of the virtual system of XYZ orthogonal coordinates of this tooth, an arrangement is determined such that the line segment connecting between point M1a for dividing the line segment connecting between the mesial pit 33a and the distal pit 33b by 49:51 and point M3b for dividing the line segment connecting between the mesial buccal cusp tip 31a and the distal lingual cusp tip 32b by 54:46 is parallel to the Z-axis, that the line segment connecting between the distal pit 33b and the mesial pit 33a is parallel to the XZ plane of the system of XYZ orthogonal coordinates, and that the condition is satisfied in the relation of X-coordinate value of mesial pit 33a<X-coordinate value of distal pit 33b.

The mesial surface, the distal surface, the buccal surface and the lower surface of the mandibular first molar tooth 30 are defined in the following relation.

The ratio of the distance of X-axis from the central fossa 33c to minimum position 34a of X-coordinate value of the mesial surface of the tooth, and the distance of X-axis from the central fossa 33c to maximum position 34b of X-coordinate value of the distal surface of the tooth is 45:65 to 55:45, and preferably 49:51 to 51:49.

The ratio of the distance of Y-axis from the central fossa 33c to maximum position 34c of Y-coordinate value of the buccal surface of the tooth, and the distance of Y-axis from the central fossa 33c to minimum position 34d of Y-coordinate value of the lingual surface of the tooth is 61:39 to 71:29, and preferably 65:35 to 67:33.

Each of the cusp tips and each of the pits of the mandibular first molar tooth 30 are defined in the following relation. The distance of line segment connecting between the mesial pit 33a and the distal pit 33b is set as S3, and the maximum width of the mandibular first premolar tooth 30 is set as W3.

The distance S3 of the line segment connecting between the mesial pit 33a and the distal pit 33b is 57 to 67% of the maximum width W3, and preferably 61 to 63%.

The distance of the line segment connecting between the mesial pit 33a and the central fossa 33c is 49 to 59% of the distance S3 of the line segment connecting between the mesial pit 33a and the distal pit 33b, and preferably 53 to 55%.

The distance of the line segment connecting between the mesial pit 33a and the mesial buccal cusp tip 31a is 46 to 56% of the distance S3 of the line segment connecting between the mesial pit 33a and the distal pit 33b, and preferably 50 to 52%.

The distance of the line segment connecting between the mesial pit 33a and the distal buccal cusp tip 31b is 70 to 80% of the distance S3 of the line segment connecting between the mesial pit 33a and the distal pit 33b, and preferably 74 to 76%.

The distance of the line segment connecting between the mesial pit 33a and the mesial lingual cusp tip 32a is 37 to 47% of the distance S3 of the line segment connecting between the mesial pit 33a and the distal pit 33b, and preferably 41 to 43%.

The distance of the line segment connecting between the mesial pit 33a and the distal lingual cusp tip 32b is 90 to 100% of the distance S3 of the line segment connecting between the mesial pit 33a and the distal pit 33b, and preferably 94 to 96%.

The distance of the line segment connecting between the mesial pit 33a and the distal cusp tip 31c is 119 to 129% of the distance S3 of the line segment connecting between the mesial pit 33a and the distal pit 33b, and preferably 123 to 125%.

The distance of the line segment connecting between the distal pit 33b and the central fossa 33c is 42 to 52% of the distance S3 of the line segment connecting between the mesial pit 33a and the distal pit 33b, and preferably 46 to 48%.

The distance of the line segment connecting between the distal pit 33b and the mesial buccal cusp tip 31a is 103 to 113% of the distance S3 of the line segment connecting between the mesial pit 33a and the distal pit 33b, and preferably 107 to 109%.

The distance of the line segment connecting between the distal pit 33b and the distal buccal cusp tip 31b is 66 to 76% of the distance S3 of the line segment connecting between the mesial pit 33a and the distal pit 33b, and preferably 70 to 72%.

The distance of the line segment connecting between the distal pit 33b and the mesial buccal cusp tip 32a is 88 to 98% of the distance S3 of the line segment connecting between the mesial pit 33a and the distal pit 33b, and preferably 92 to 94%.

The distance of the line segment connecting between the distal pit 33b and the distal lingual cusp tip 32b is 42 to 52% of the distance S3 of the line segment connecting between the mesial pit 33a and the distal pit 33b, and preferably 46 to 48%.

The distance of the line segment connecting between the distal pit 33b and the distal cusp tip 31c is 41 to 51% of the distance S3 of the line segment connecting between the mesial pit 33a and the distal pit 33b, and preferably 45 to 47%.

The distance of the line segment connecting between the central fossa 33c and the mesial buccal cusp tip 31a is 68 to 78% of the distance S3 of the line segment connecting between the mesial pit 33a and the distal pit 33b, and preferably 72 to 74%.

The distance of the line segment connecting between the central fossa 33c and the distal buccal cusp tip 31b is 52 to 62% of the distance S3 of the line segment connecting between the mesial pit 33a and the distal pit 33b, and preferably 56 to 58%.

The distance of the line segment connecting between the central fossa 33c and the mesial lingual cusp tip 32a is 46 to 56% of the distance S3 of the line segment connecting between the mesial pit 33a and the distal pit 33b, and preferably 50 to 52%.

The distance of the line segment connecting between the central fossa 33c and the distal lingual cusp tip 32b is 44 to 54% of the distance S3 of the line segment connecting between the mesial pit 33a and the distal pit 33b, and preferably 48 to 50%.

The distance of the line segment connecting between the central fossa 33c and the distal cusp tip 31c is 73 to 83% of the distance S3 of the line segment connecting between the mesial pit 33a and the distal pit 33b, and preferably 77 to 79%.

The distance of the line segment connecting between the mesial buccal cusp tip 31a and the distal buccal cusp tip 31b is 43 to 53% of the distance S3 of the line segment connecting between the mesial pit 33a and the distal pit 33b, and preferably 47 to 49%.

The distance of the line segment connecting between the mesial buccal cusp tip 31a and the mesial lingual cusp tip 32a is 70 to 80% of the distance S3 of the line segment connecting between the mesial pit 33a and the distal pit 33b, and preferably 74 to 76%.

The distance of the line segment connecting between the mesial buccal cusp tip 31a and the distal lingual cusp tip 32b is 106 to 116% of the distance S3 of the line segment connecting between the mesial pit 33a and the distal pit 33b, and preferably 110 to 112%.

The distance of the line segment connecting between the mesial buccal cusp tip 31a and the distal cusp tip 31c is 106 to 116% of the distance S3 of the line segment connecting between the mesial pit 33a and the distal pit 33b, and preferably 110 to 112%.

The distance of the line segment connecting between the distal buccal cusp tip 31b and the mesial lingual cusp tip 32a is 80 to 90% of the distance S3 of the line segment connecting between the mesial pit 33a and the distal pit 33b, and preferably 84 to 86%.

The distance of the line segment connecting between the distal buccal cusp tip 31b and the distal lingual cusp tip 32b is 81 to 91% of the distance S3 of the line segment connecting between the mesial pit 33a and the distal pit 33b, and preferably 85 to 87%.

The distance of the line segment connecting between the distal buccal cusp tip 31b and the distal cusp tip 31c is 58 to 68% of the distance S3 of the line segment connecting between the mesial pit 33a and the distal pit 33b, and preferably 62 to 64%.

The distance of the line segment connecting between the mesial lingual cusp tip 32a and the distal lingual cusp tip 32b is 64 to 74% of the distance S3 of the line segment connecting between the mesial pit 33a and the distal pit 33b, and preferably 68 to 70%.

The distance of the line segment connecting between the mesial lingual cusp tip 32a and the distal cusp tip 31c is 115 to 125% of the distance S3 of the line segment connecting between the mesial pit 33a and the distal pit 33b, and preferably 119 to 121%.

The distance of the line segment connecting between the distal cusp tip 31c and the distal lingual cusp tip 32b is 72 to 82% of the distance S3 of the line segment connecting between the mesial pit 33a and the distal pit 33b, and preferably 76 to 78%.

<Artificial Tooth of Maxillary First Molar Tooth>

Figure 10:
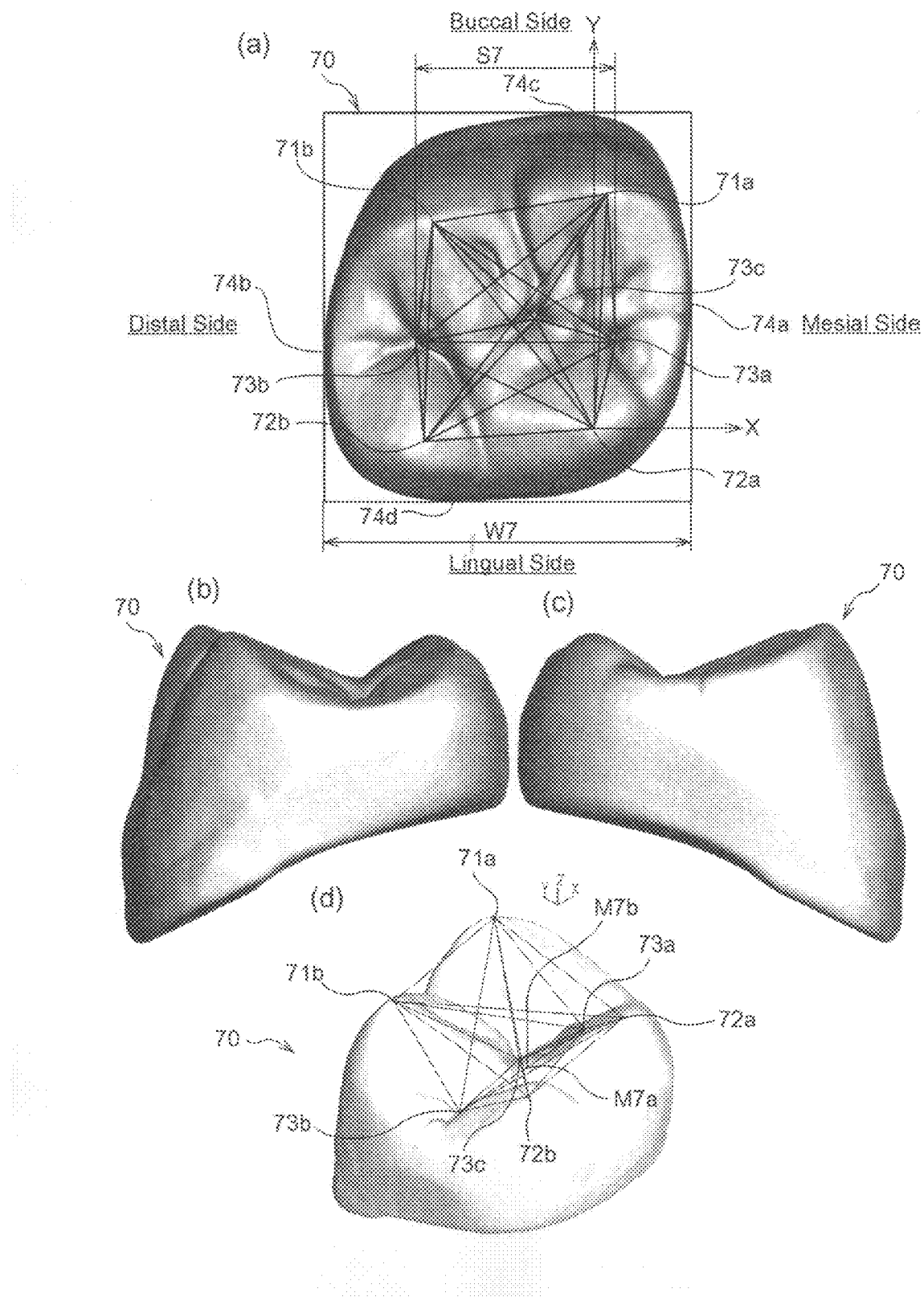
FIG. 10(a) shows an occlusal surface view of the maxillary first molar tooth.
FIG. 10(b) shows a mesial surface view of the maxillary first molar tooth.
FIG. 10(c) shows a distal surface view of the maxillary first molar tooth.
FIG. 10(d) shows an oblique view of the maxillary first molar tooth.

FIG. 10 shows an artificial tooth of a maxillary first molar tooth 70. In the figure, the left side is the distal side, the right side is the mesial side, the upside is the buccal side, and the downside is the lingual side.

The artificial tooth of the maxillary first molar tooth 70 has a mesial buccal cusp tip 71a, a distal buccal cusp tip 71b, a mesial lingual cusp tip 72a, a distal lingual cusp tip 72b, a mesial pit 73a, a distal pit 73b, and a central fossa 73c.

In order to clarify the three-dimensional positional relation of the cusp tips and the pits, in an example of the right side, when supposing the mesial lingual cusp tip 72a to be the origin of the virtual system of XYZ orthogonal coordinates of this tooth, an arrangement is determined such that the line segment connecting between a point M7a for dividing the line segment connecting between the mesial pit 73a and the distal pit 73b by 46:54 and a point M7b for dividing the line segment connecting between the distal buccal cusp tip 71b and the mesial lingual cusp tip 72a by 58:42 is parallel to the Z-axis, that the line segment connecting between the distal pit 73b and the mesial pit 73a is parallel to the XZ plane of the system of XYZ orthogonal coordinates, and that the condition is satisfied in the relation of X-coordinate value of mesial pit 73a>X-coordinate value of distal pit 73b.

The mesial surface, the distal surface, the buccal surface and the lower surface of the maxillary first molar tooth 70 are defined in the following relation.

The ratio of the distance of X-axis from the mesial lingual cusp tip 72a to maximum position 74a of X-coordinate value of the mesial surface of the tooth, and the distance of X-axis from the mesial lingual cusp tip 72a to minimum position 74b of X-coordinate value of the distal surface of the tooth is 22:78 to 32:68, and preferably 26:74 to 28:72.

The ratio of the distance of Y-axis from the mesial lingual cusp tip 72a to maximum position 74c of Y-coordinate value of the buccal surface of the tooth, and the distance of Y-axis from the mesial lingual cusp tip 72a to minimum position 74d of Y-coordinate value of the lingual surface of the tooth is 76:24 to 86:14, and preferably 80:20 to 82:18.

Each of the cusp tips and each of the pits of the maxillary first molar tooth 70 are defined in the following relation. Here, the distance of line segment connecting between the mesial pit 73a and the distal pit 73b is set as S7, and the maximum width of the maxillary first premolar tooth 70 is set as W7.

The distance S7 of the line segment connecting between the mesial pit 73a and the distal pit 73b is 57 to 67% of the maximum width W7, and preferably 61 to 63%.

The distance of the line segment connecting between the mesial pit 73a and the central fossa 73c is 37 to 47% of the distance S7 of the line segment connecting between the mesial pit 73a and the distal pit 73b, and preferably 41 to 43%.

The distance of the line segment connecting between the mesial pit 73a and the mesial buccal cusp tip 71a is 78 to 88% of the distance S7 of the line segment connecting between the mesial pit 73a and the distal pit 73b, and preferably 82 to 84%.

The distance of the line segment connecting between the mesial pit 73a and the distal buccal cusp tip 71b is 111 to 121% of the distance S7 of the line segment connecting between the mesial pit 73a and the distal pit 73b, and preferably 115 to 117%.

The distance of the line segment connecting between the mesial pit 73a and the mesial lingual cusp tip 72a is 51 to 61% of the distance S7 of the line segment connecting between the mesial pit 73a and the distal pit 73b, and preferably 55 to 57%.

The distance of the line segment connecting between the mesial pit 73a and the distal lingual cusp tip 72b is 109 to 119% of the distance S7 of the line segment connecting between the mesial pit 73a and the distal pit 73b, and preferably 113 to 115%.

The distance of the line segment connecting between the distal pit 73b and the central fossa 73c is 56 to 66% of the distance S7 of the line segment connecting between the mesial pit 73a and the distal pit 73b, and preferably 60 to 62%.

The distance of the line segment connecting between the distal pit 73b and the mesial buccal cusp tip 71a is 128 to 138% of the distance S7 of the line segment connecting between the mesial pit 73a and the distal pit 73b, and preferably 132 to 134%.

The distance of the line segment connecting between the distal pit 73b and the distal buccal cusp tip 71b is 68 to 78% of the distance S7 of the line segment connecting between the mesial pit 73a and the distal pit 73b, and preferably 72 to 75%.

The distance of the line segment connecting between the distal pit 73b and the mesial lingual cusp tip 72a is 102 to 112% of the distance S7 of the line segment connecting between the mesial pit 73a and the distal pit 73b, and preferably 106 to 108%.

The distance of the line segment connecting between the distal pit 73b and the distal lingual cusp tip 72b is 58 to 68% of the distance S7 of the line segment connecting between the mesial pit 73a and the distal pit 73b, and preferably 62 to 64%.

The distance of the line segment connecting between the central fossa 73c and the mesial buccal cusp tip 71a is 82 to 92% of the distance S7 of the line segment connecting between the mesial pit 73a and the distal pit 73b, and preferably 86 to 88%.

The distance of the line segment connecting between the central fossa 73c and the distal buccal cusp tip 71b is 78 to 88% of the distance S7 of the line segment connecting between the mesial pit 73a and the distal pit 73b, and preferably 82 to 84%.

The distance of the line segment connecting between the central fossa 73c and the mesial lingual cusp tip 72a is 70 to 80% of the distance S7 of the line segment connecting between the mesial pit 73a and the distal pit 73b, and preferably 74 to 76%.

The distance of the line segment connecting between the central fossa 73c and the distal lingual cusp tip 72b is 88 to 98% of the distance S7 of the line segment connecting between the mesial pit 73a and the distal pit 73b, and preferably 92 to 94%.

The distance of the line segment connecting between the mesial buccal cusp tip 71a and the distal buccal cusp tip 71b is 90 to 100% of the distance S7 of the line segment connecting between the mesial pit 73a and the distal pit 73b, and preferably 94 to 96%.

The distance of the line segment connecting between the mesial buccal cusp tip 71a and the mesial lingual cusp tip 72a is 112 to 122% of the distance S7 of the line segment connecting between the mesial pit 73a and the distal pit 73b, and preferably 116 to 118%.

The distance of the line segment connecting between the mesial buccal cusp tip 71a and the distal lingual cusp tip 72b is 154 to 164% of the distance S7 of the line segment connecting between the mesial pit 73a and the distal pit 73b, and preferably 158 to 160%.

The distance of the line segment connecting between the distal buccal cusp tip 71b and the mesial lingual cusp tip 72a is 125 to 135% of the distance S7 of the line segment connecting between the mesial pit 73a and the distal pit 73b, and preferably 129 to 131%.

The distance of the line segment connecting between the distal buccal cusp tip 71b and the distal lingual cusp tip 72b is 106 to 116% of the distance S7 of the line segment connecting between the mesial pit 73a and the distal pit 73b, and preferably 110 to 112%.

The distance of the line segment connecting between the mesial lingual cusp tip 72a and the distal lingual cusp tip 72b is 81 to 91% of the distance S7 of the line segment connecting between the mesial pit 73a and the distal pit 73b, and preferably 85 to 87%.

<A Set of Artificial Teeth of Mandibular First Molar Tooth and Maxillary First Molar Tooth>

Figure 11:
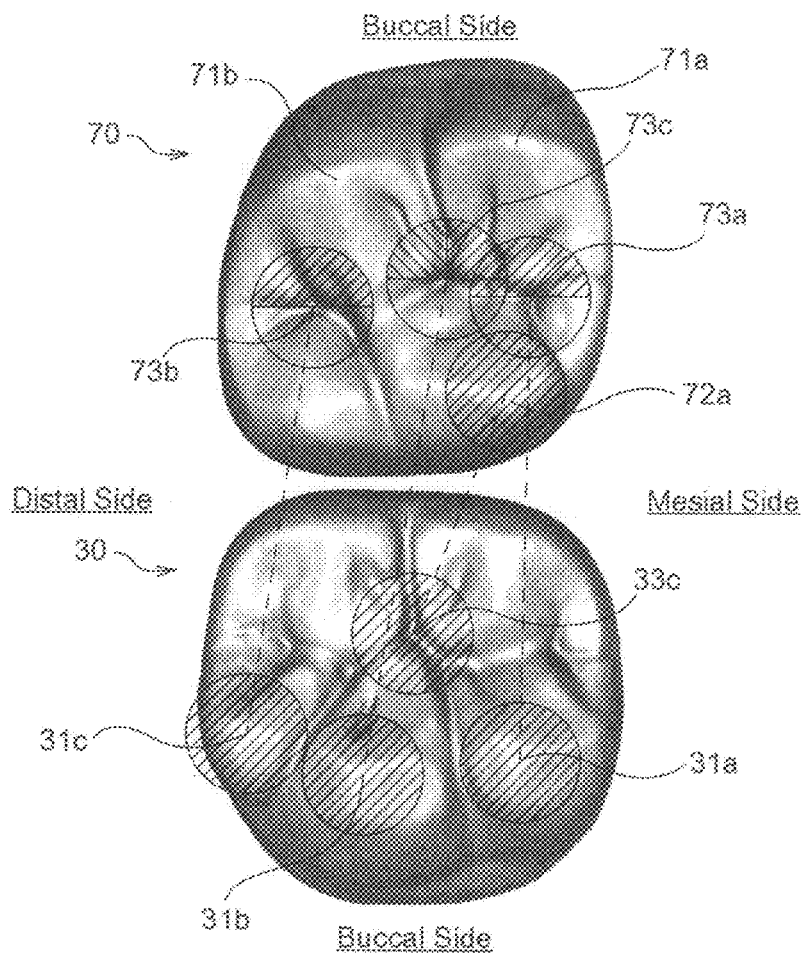
FIG. 11 shows an occlusal surface view of the mandibular first molar tooth and the maxillary first molar tooth.
Figure 12:
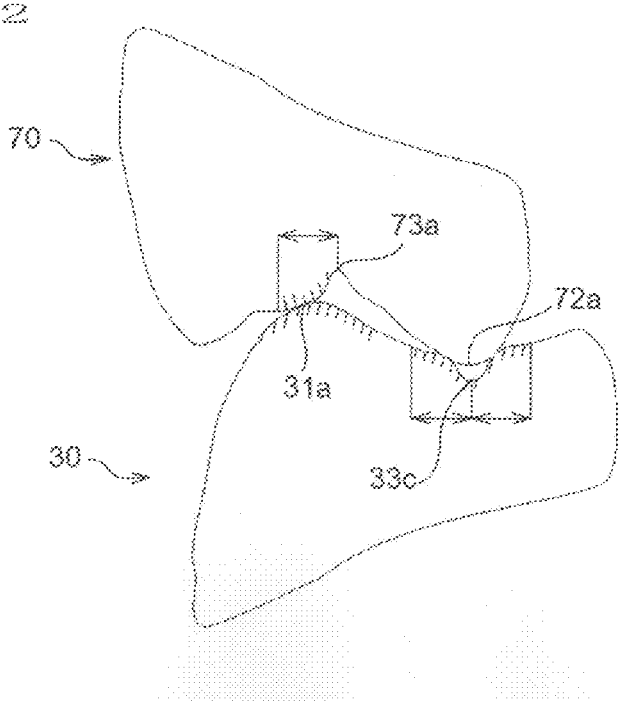
FIG. 12 shows a contact state sectional view of the mandibular first molar tooth and the maxillary first molar tooth.

FIG. 11 and FIG. 12 show the set of artificial teeth of the mandibular first molar tooth 30 and the maxillary first molar tooth 70.

In the set of artificial teeth of the mandibular first molar tooth 30 and the maxillary first molar tooth 70, the occlusal surface within 1.50 mm in radius from the central fossa 33c of the mandibular first molar tooth 30 has one or more contact points with the occlusal surface within 1.50 mm in radius from the mesial lingual cusp tip 72a of the maxillary first molar tooth 70.

Preferably, there are three contact points in total, that is, one contact point between the distal buccal cusp inner bevel within 1.00 mm from the central fossa 33c of the mandibular first molar tooth 30 and the lingual cusp inner bevel within 1.00 mm from the mesial lingual cusp tip 72a of the maxillary first molar tooth 70, one contact point between the inner bevel of the mesial lingual cusp within 1.00 mm from the central fossa 33c of the mandibular first molar tooth 30 and the outer bevel from the mesial occlusal margin within 1.00 mm from the mesial lingual cusp tip 72a of the maxillary first molar tooth 70, and one contact point between the inner bevel of the distal lingual cusp within 1.00 mm from the central fossa 33c of the mandibular first molar tooth 30 and the outer bevel from the distal occlusal margin within 1.00 mm from the mesial lingual cusp tip 72a of the maxillary first molar tooth 70.

Accordingly, contact points are formed in a small region of the occlusal surface, and therefore it is easy to check the occlusal state, and effects of efficient arrangement can be expected.

Further, in the set of artificial teeth of the mandibular first molar tooth 30 and the maxillary first molar tooth 70, the occlusal surface within 1.50 mm in radius from the mesial buccal cusp tip 31a of the mandibular first molar tooth 30 has one or more contact points with the occlusal surface within 1.50 mm from the mesial pit 73a of the maxillary first molar tooth 70, the occlusal surface within 1.50 mm in radius from the distal buccal cusp tip 31b of the mandibular first molar tooth 30 has one or more contact points with the occlusal surface within 1.50 mm from the central fossa 73c of the maxillary first molar tooth 70, and the occlusal surface within 1.50 mm from the distal cusp tip 31c of the mandibular first molar tooth 30 and the occlusal surface within 1.50 mm from the distal pit 73b of the maxillary first molar tooth 70 have one or more contact points.

Preferably, there are four contact points in total, that is, one contact point between the outer bevel within 1.00 in radius from the mesial buccal cusp tip 31a of the mandibular first molar tooth 30 and the buccal inner bevel within 1.00 mm from the mesial pit 73a of the maxillary first molar tooth 70, two contact points between the outer bevel within 1.00 mm in radius from the distal buccal cusp tip 31b of the mandibular first molar tooth 30 and the inner bevel of the mesial buccal cusp and the inner bevel of the distal buccal cusp within 1.00 mm in radius from the central fossa 73c of the maxillary first molar tooth 70, and one contact point between the outer bevel within 1.00 mm from the distal cusp tip 31c of the mandibular first molar tooth 30 and the buccal inner bevel within 1.00 mm from the distal pit 73b of the maxillary first premolar tooth 70.

Accordingly, contact points are formed in a small region of the occlusal surface, and therefore it is easy to check the occlusal state, and effects of efficient arrangement can be expected.

<Artificial Tooth of Mandibular Second Molar Tooth>

Figure 13:
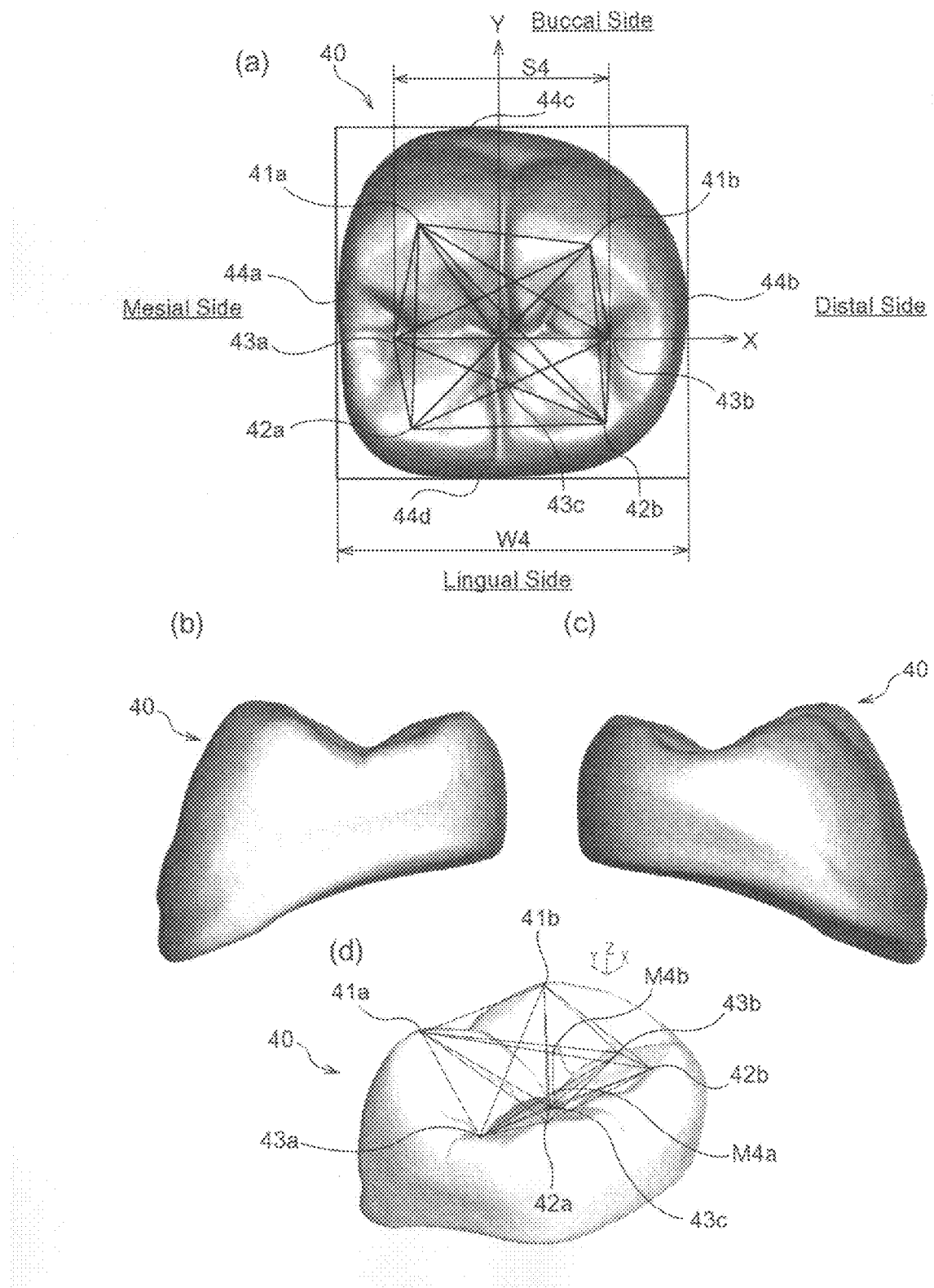
FIG. 13(a) shows an occlusal surface view of the mandibular second molar tooth.
FIG. 13(b) shows a mesial surface view of the mandibular second molar tooth.
FIG. 13(c) shows a distal surface view of the mandibular second molar tooth.
FIG. 13(d) shows an oblique view of the mandibular second molar tooth.

FIG. 13 shows an artificial tooth of a mandibular second molar tooth 40. In the figure, the left side is the mesial side, the right side is the distal side, the upside is the buccal side, and the downside is the lingual side.

The artificial tooth of the mandibular second molar tooth 40 has a mesial buccal cusp tip 41a, a distal buccal cusp tip 41b, a mesial lingual cusp tip 42a, a distal lingual cusp tip 42b, a mesial pit 43a, a distal pit 43b, and a central fossa 43c.

In order to clarify the three-dimensional positional relation of the cusp tips and the pits, in an example of the right side, when supposing the central fossa 43c to be the origin of the virtual system of XYZ orthogonal coordinates of this tooth, an arrangement is determined such that the line segment connecting between a point M4a for dividing the line segment connecting between the mesial pit 43a and the distal pit 43b by 53:47 and a point M4b for dividing the line segment connecting between the mesial buccal cusp tip 41a and the distal lingual cusp tip 42b by 57:42 is parallel to the Z-axis, that the line segment connecting between the distal pit 43b and the mesial pit 43a is parallel to the XZ plane of the XZ plane of the system of XYZ orthogonal coordinates, and that the condition is determined in the relation of X-coordinate value of mesial pit 43a<X-coordinate value of distal pit 43b.

The mesial surface, the distal surface, the buccal surface and the lower surface of the mandibular second molar tooth 40 are defined in the following relation.

The ratio of the distance of X-axis from the central fossa 43c to minimum position 44a of X-coordinate value of the mesial surface of the tooth, and the distance of X-axis from the central fossa 43c to maximum position 44b of X-coordinate value of the distal surface of the tooth is 40:60 to 50:50, and preferably 44:56 to 46:54.

The ratio of the distance of Y-axis from the central fossa 43c to maximum position 44c of Y-coordinate value of the buccal surface of the tooth, and the distance of Y-axis from the central fossa 43c to minimum position 44d of Y-coordinate value of the lingual surface of the tooth is 56:44 to 66:34, and preferably 60:40 to 62:38.

Each of the cusp tips and each of the pits of the mandibular second molar tooth 40 are defined in the following relation. Here, the distance of line segment connecting between the mesial pit 43a and the distal pit 43b is set as S4, and the maximum width of the mandibular second molar tooth 40 is set as W4.

The distance S4 of the line segment connecting between the mesial pit 43a and the distal pit 43b is 56 to 66% of the maximum width W4, and preferably 40 to 42%.

The distance of the line segment connecting between the mesial pit 43a and the central fossa 43c is 43 to 53% of the distance S4 of the line segment connecting between the mesial pit 43a and the distal pit 43b, and preferably 47 to 49%.

The distance of the line segment connecting between the mesial pit 43a and the mesial buccal cusp tip 41a is 58 to 68% of the distance S4 of the line segment connecting between the mesial pit 43a and the distal pit 43b, and preferably 62 to 64%.

The distance of the line segment connecting between the mesial pit 43a and the distal buccal cusp tip 41b is 99 to 108% of the distance S4 of the line segment connecting between the mesial pit 43a and the distal pit 43b, and preferably 102 to 104%.

The distance of the line segment connecting between the mesial pit 43a and the mesial lingual cusp tip 42a is 44 to 54% of the distance S4 of the line segment connecting between the mesial pit 43a and the distal pit 43b, and preferably 48 to 50%.

The distance of the line segment connecting between the mesial pit 43a and the distal lingual cusp tip 42b is 90 to 80% of the distance S4 of the line segment connecting between the mesial pit 43a and the distal pit 43b, and preferably 94 to 96%.

The distance of the line segment connecting between the distal pit 43b and the central fossa 43c is 48 to 58% of the distance S4 of the line segment connecting between the mesial pit 43a and the distal pit 43b, and preferably 52 to 54%.

The distance of the line segment connecting between the distal pit 43b and the mesial buccal cusp tip 41a is 102 to 112% of the distance S4 of the line segment connecting between the mesial pit 43a and the distal pit 43b, and preferably 106 to 108%.

The distance of the line segment connecting between the distal pit 43b and the distal buccal cusp tip 41b is 46 to 56% of the distance S4 of the line segment connecting between the mesial pit 43a and the distal pit 43b, and preferably 50 to 52%.

The distance of the line segment connecting between the distal pit 43b and the mesial lingual cusp tip 42a is 99 to 109% of the distance S4 of the line segment connecting between the mesial pit 43a and the distal pit 43b, and preferably 103 to 105%.

The distance of the line segment connecting between the distal pit 43*b* and the distal lingual cusp tip 42*b* is 42 to 52% of the distance S4 of the line segment connecting between the mesial pit 43*a* and the distal pit 43*b*, and preferably 46 to 48%.

The distance of the line segment connecting between the central fossa 43*c* and the mesial buccal cusp tip 41*a* is 70 to 80% of the distance S4 of the line segment connecting between the mesial pit 43*a* and the distal pit 43*b*, and preferably 74 to 76%.

The distance of the line segment connecting between the central fossa 43*c* and the distal buccal cusp tip 41*b* is 64 to 74% of the distance S4 of the line segment connecting between the mesial pit 43*a* and the distal pit 43*b*, and preferably 68 to 70%.

The distance of the line segment connecting between the central fossa 43*c* and the mesial lingual cusp tip 42*a* is 57 to 67% of the distance S4 of the line segment connecting between the mesial pit 43*a* and the distal pit 43*b*, and preferably 61 to 63%.

The distance of the line segment connecting between the central fossa 43*c* and the distal lingual cusp tip 42*b* is 52 to 62% of the distance S4 of the line segment connecting between the mesial pit 43*a* and the distal pit 43*b*, and preferably 56 to 58%.

The distance of the line segment connecting between the mesial buccal cusp tip 41*a* and the distal buccal cusp tip 41*b* is 74 to 84% of the distance S4 of the line segment connecting between the mesial pit 43*a* and the distal pit 43*b*, and preferably 78 to 80%.

The distance of the line segment connecting between the mesial buccal cusp tip 41*a* and the mesial lingual cusp tip 42*a* is 89 to 99% of the distance S4 of the line segment connecting between the mesial pit 43*a* and the distal pit 43*b*, and preferably 93 to 96%.

The distance of the line segment connecting between the mesial buccal cusp tip 41*a* and the distal lingual cusp tip 42*b* is 113 to 123% of the distance S4 of the line segment connecting between the mesial pit 43*a* and the distal pit 43*b*, and preferably 117 to 119%.

The distance of the line segment connecting between the distal buccal cusp tip 41*b* and the mesial lingual cusp tip 42*a* is 112 to 122% of the distance S4 of the line segment connecting between the mesial pit 43*a* and the distal pit 43*b*, and preferably 116 to 118%.

The distance of the line segment connecting between the distal buccal cusp tip 41*b* and the distal lingual cusp tip 42*b* is 79 to 89% of the distance S4 of the line segment connecting between the mesial pit 43*a* and the distal pit 43*b*, and preferably 83 to 85%.

The distance of the line segment connecting between the mesial lingual cusp tip 42*a* and the distal lingual cusp tip 42*b* is 71 to 81% of the distance S4 of the line segment connecting between the mesial pit 43*a* and the distal pit 43*b*, and preferably 75 to 77%.

<Artificial Tooth of Maxillary Second Molar Tooth>

Figure 14:
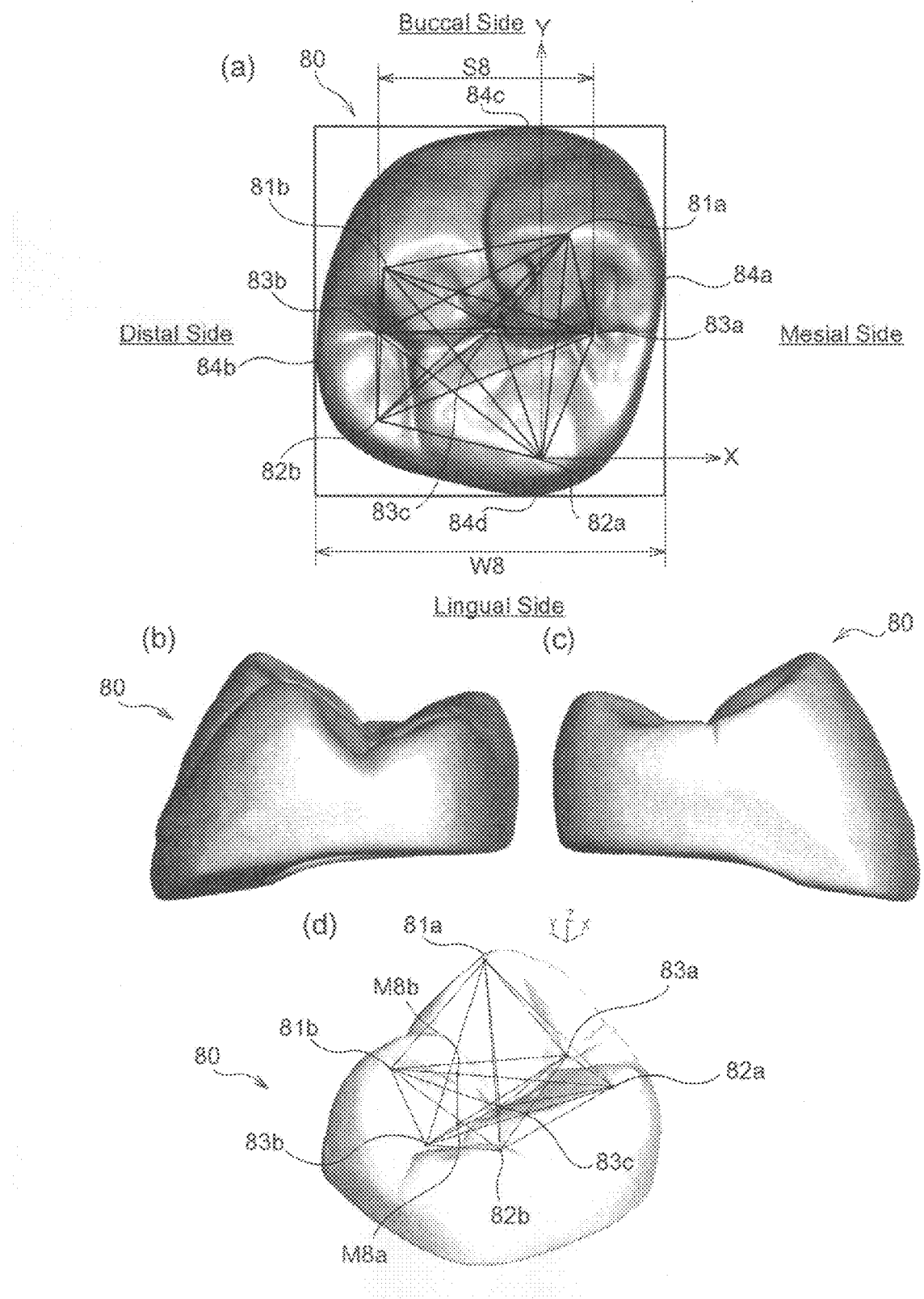
FIG. 14(a) shows an occlusal surface view of the maxillary second molar tooth.
FIG. 14(b) shows a mesial surface view of the maxillary second molar tooth.
FIG. 14(c) shows a distal surface view of the maxillary second molar tooth.
FIG. 14(d) shows an oblique view of the maxillary second molar tooth.

FIG. 14 shows an artificial tooth of a maxillary second molar tooth 80. In the figure, the left side is the distal side, the right side is the mesial side, the upside is the buccal side, and the downside is the lingual side.

The artificial tooth of the maxillary second molar tooth 80 has a mesial buccal cusp tip 81*a*, a distal buccal cusp tip 81*b*, a mesial lingual cusp tip 82*a*, a distal lingual cusp tip 82*b*, a mesial pit 83*a*, a distal pit 83*b*, and a central fossa 83*c*.

In order to clarify the three-dimensional positional relation of the cusp tips and the pits, in an example of the right side, when supposing the mesial lingual cusp tip 82*a* to be the origin of the virtual system of XYZ orthogonal coordinates of this tooth, an arrangement is determined such that the line segment connecting between a point M8*a* for dividing the line segment connecting between the mesial pit 83*a* and the distal pit 83*b* by 78:22 and a point M8*b* for dividing the line segment connecting between the distal buccal cusp tip 81*b* and the mesial lingual cusp tip 82*a* by 30:70 is parallel to the Z-axis of the system of XYZ orthogonal coordinates, that the segment connecting between the distal pit 83*b* and the mesial pit 83*a* is parallel to the XZ plane of the system of XYZ orthogonal coordinates, and that the condition is satisfied in the relation of X-coordinate value of mesial pit 83*a*>X-coordinate value of distal pit 83*b*.

The mesial surface, the distal surface, the buccal surface and the lower surface of the maxillary second molar tooth 80 are defined in the following relation.

The ratio of the distance of X-axis from the mesial lingual cusp tip 82*a* to maximum position 84*a* of X-coordinate value of the mesial surface of the tooth, and the distance of X-axis from the mesial lingual cusp tip 82*a* to minimum position 84*b* of X-coordinate value of the distal surface of the tooth is 32:68 to 42:58, and preferably 36:64 to 38:62.

The ratio of the distance of Y-axis from the mesial lingual cusp tip 82*a* to maximum position 84*c* of Y-coordinate value of the buccal surface of the tooth, and the distance of Y-axis from the mesial lingual cusp tip 82*a* to minimum position 84*d* of Y-coordinate value of the lingual surface of the tooth is 85:15 to 95:5, and preferably 89:11 to 91:9.

Each of the cusp tips and each of the pits of the maxillary second molar tooth 80 are defined in the following relation. The distance of line segment connecting between the mesial pit 83*a* and the distal pit 83*b* is set as S8, and the maximum width of the maxillary second molar tooth 80 is set as W8.

The distance S8 of the line segment connecting between the mesial pit 83*a* and the central fossa 83*c* is 40 to 50% of the maximum width W8, and preferably 44 to 46%.

The distance of the line segment connecting between the mesial pit 83*a* and the central fossa 83*c* is 42 to 52% of the distance S8 of the line segment connecting between the mesial pit 83*a* and the distal pit 83*b*, and preferably 46 to 48%.

The distance of the line segment connecting between the mesial pit 83*a* and the mesial buccal cusp tip 81*a* is 58 to 68% of the distance S8 of the line segment connecting between the mesial pit 83*a* and the distal pit 83*b*, and preferably 62 to 64%.

The distance of the line segment connecting between the mesial pit 83*a* and the distal buccal cusp tip 81*b* is 101 to 111% of the distance S8 of the line segment connecting between the mesial pit 83*a* and the distal pit 83*b*, and preferably 105 to 107%.

The distance of the line segment connecting between the mesial pit 83*a* and the mesial lingual cusp tip 82*a* is 65 to 75% of the distance S8 of the line segment connecting between the mesial pit 83*a* and the distal pit 83*b*, and preferably 69 to 71%.

The distance of the line segment connecting between the mesial pit 83*a* and the distal lingual cusp tip 82*b* is 102 to 112% of the distance S8 of the line segment connecting between the mesial pit 83*a* and the distal pit 83*b*, and preferably 106 to 108%.

The distance of the line segment connecting between the distal pit 83*b* and the central fossa 83*c* is 49 to 59% of the distance S8 of the line segment connecting between the mesial pit 83*a* and the distal pit 83*b*, and preferably 53 to 55%.

The distance of the line segment connecting between the distal pit 83b and the mesial buccal cusp tip 81a is 103 to 113% of the distance S8 of the line segment connecting between the mesial pit 83a and the distal pit 83b, and preferably 107 to 109%.

The distance of the line segment connecting between the distal pit 83b and the distal buccal cusp tip 81b is 37 to 47% of the distance S8 of the line segment connecting between the mesial pit 83a and the distal pit 83b, and preferably 41 to 43%.

The distance of the line segment connecting between the distal pit 83b and the mesial lingual cusp tip 82a is 94 to 104% of the distance S8 of the line segment connecting between the mesial pit 83a and the distal pit 83b, and preferably 98 to 100%.

The distance of the line segment connecting between the distal pit 83b and the distal lingual cusp tip 82b is 46 to 56% of the distance S8 of the line segment connecting between the mesial pit 83a and the distal pit 83b, and preferably 50 to 52%.

The distance of the line segment connecting between the central fossa 83c and the mesial buccal cusp tip 81a is 70 to 80% of the distance S8 of the line segment connecting between the mesial pit 83a and the distal pit 83b, and preferably 74 to 76%.

The distance of the line segment connecting between the central fossa 83c and the distal buccal cusp tip 81b is 65 to 75% of the distance S8 of the line segment connecting between the mesial pit 83a and the distal pit 83b, and preferably 69 to 71%.

The distance of the line segment connecting between the central fossa 83c and the mesial lingual cusp tip 82a is 68 to 78% of the distance S8 of the line segment connecting between the mesial pit 83a and the distal pit 83b, and preferably 72 to 74%.

The distance of the line segment connecting between the central fossa 83c and the distal lingual cusp tip 82b is 68 to 78% of the distance S8 of the line segment connecting between the mesial pit 83a and the distal pit 83b, and preferably 72 to 74%.

The distance of the line segment connecting between the mesial buccal cusp tip 81a and the distal buccal cusp tip 81b is 85 to 95% of the distance S8 of the line segment connecting between the mesial pit 83a and the distal pit 83b, and preferably 88 to 90%.

The distance of the line segment connecting between the mesial buccal cusp tip 81a and the mesial lingual cusp tip 82a is 102 to 112% of the distance S8 of the line segment connecting between the mesial pit 83a and the distal pit 83b, and preferably 106 to 108%.

The distance of the line segment connecting between the mesial buccal cusp tip 81a and the distal lingual cusp tip 82b is 122 to 132% of the distance S8 of the line segment connecting between the mesial pit 83a and the distal pit 83b, and preferably 126 to 128%.

The distance of the line segment connecting between the distal buccal cusp tip 81b and the mesial lingual cusp tip 82a is 107 to 117% of the distance S8 of the line segment connecting between the mesial pit 83a and the distal pit 83b, and preferably 111 to 113%.

The distance of the line segment connecting between the distal buccal cusp tip 81b and the distal lingual cusp tip 82b is 70 to 80% of the distance S8 of the line segment connecting between the mesial pit 83a and the distal pit 83b, and preferably 74 to 76%.

The distance of the line segment connecting between the mesial lingual cusp tip 82a and the distal lingual cusp tip 82b is 65 to 75% of the distance S8 of the line segment connecting between the mesial pit 83a and the distal pit 83b, and preferably 69 to 71%.

<A Set of Artificial Teeth of Mandibular Second Molar Tooth and Maxillary Second Molar Tooth>

Figure 15:
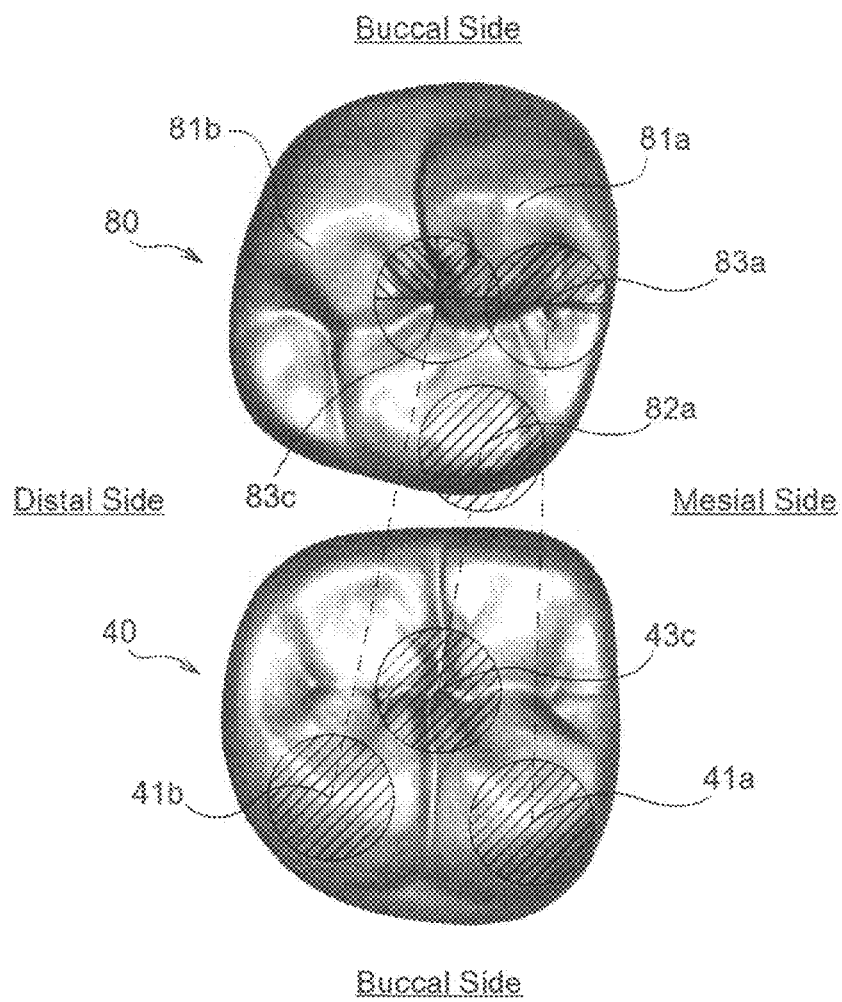
FIG. 15 shows an occlusal surface view of the mandibular second molar tooth and the maxillary second molar tooth.
Figure 16:
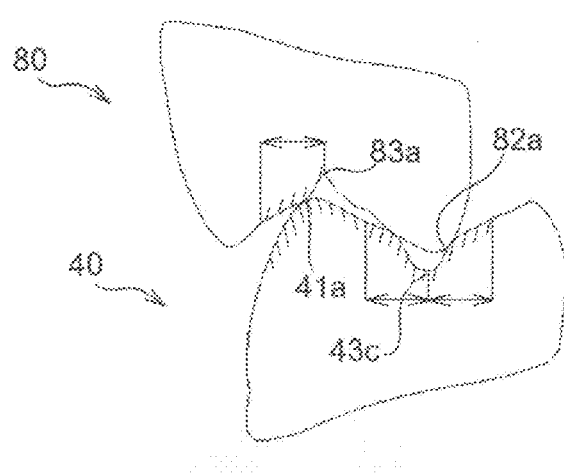
FIG. 16 shows a contact state sectional view of the mandibular second molar tooth and the maxillary second molar tooth.

FIG. 15 and FIG. 16 show the set of artificial teeth of a mandibular second molar tooth 40 and a maxillary second molar tooth 80.

In the set of artificial teeth of a mandibular second molar tooth 40 and a maxillary second molar tooth 80, the occlusal surface within 1.50 mm in radius from the central fossa 43c of the mandibular second molar tooth 40 and the occlusal surface within 1.50 mm in radius from the mesial lingual cusp tip 82a of the maxillary first molar tooth 80 have at least one contact point.

Preferably, there are three contact points in total, that is, one contact point between the buccal inner bevel within 1.00 mm in radius from the central fossa 43c of the mandibular second molar tooth 40 and the lingual inner bevel within 1.00 mm in radius from the mesial lingual cusp tip 82a of the maxillary second molar tooth 80, one contact point between the mesial lingual cusp inner bevel within 1.00 mm in radius from the central fossa 43c of the mandibular second molar tooth 40 and the outer bevel within 1.00 min radius from the mesial lingual cusp tip 82a of the maxillary second molar tooth 80, and one contact point between the distal lingual cusp inner bevel within 1.00 mm in radius from the central fossa 43c of the mandibular second premolar tooth 40 and the outer bevel within 1.00 mm in radius from the mesial lingual cusp tip 82a of the maxillary first molar tooth 80.

Accordingly, contact points are formed in a small region of the occlusal surface, and therefore it is easy to check the occlusal state, and effects of efficient arrangement can be expected.

Further, in the set of artificial teeth of mandibular second molar tooth 40 and maxillary second molar tooth 80, the occlusal surface within 1.50 mm in radius from the mesial buccal cusp tip 41a of the mandibular second molar tooth 40 has one or more contact points with the occlusal surface within 1.50 mm from the mesial pit 83a of the maxillary second molar tooth 80, and the occlusal surface within 1.50 mm in radius from the distal buccal cusp tip 41b of the mandibular second molar tooth 40 has one or more contact points with the occlusal surface within 1.50 mm from the central fossa 83c of the maxillary second molar tooth 80.

Preferably, there are three contact points in total, that is, one contact point between the outer bevel within 1.00 in radius from the mesial buccal cusp tip 41a of the mandibular second molar tooth 40 and the buccal inner bevel within 1.00 mm from the mesial pit 83a of the maxillary second molar tooth 80, one contact point between the outer bevel within 1.00 mm in radius from the distal buccal cusp tip 41b of the mandibular second molar tooth 40 and the mesial buccal cusp inner bevel within 1.00 mm from the central fossa 83c of the maxillary second molar tooth 80, and one contact point between the outer bevel within 1.00 mm in radius from the distal buccal cusp tip 41b of the mandibular second molar tooth 40 and the distal buccal cusp inner bevel within 1.00 mm from the central fossa 83c of the maxillary second molar tooth 80.

Accordingly, contact points are formed in a small region of the occlusal surface, and therefore it is easy to check the occlusal state, and effects of efficient arrangement can be expected.

<A Set of Artificial Teeth of Mandibular Molar Teeth>

FIG. 17 (a) shows a set of artificial teeth of mandibular molar teeth. In the figure, the left side is the distal side, the right side is the mesial side, the upside is the lingual side, and the downside is the buccal side.

The set of artificial teeth of mandibular molar teeth has the artificial teeth composed of a mandibular first premolar tooth 10, a mandibular second premolar tooth 20, a mandibular first molar tooth 30, and a mandibular second molar tooth 40.

The maximum width W2 of the artificial tooth of the mandibular second premolar tooth 20 is 102 to 112% of the maximum width W1 of the artificial tooth of the mandibular first premolar tooth 10.

The maximum width W3 of the artificial tooth of the mandibular first molar tooth 30 is 144 to 154% of the maximum width W1 of the artificial tooth of the mandibular first premolar tooth 10.

The maximum width W4 of the artificial tooth of the mandibular second molar tooth 40 is 125 to 135% of the maximum width W1 of the artificial tooth of the mandibular first premolar tooth 10.

The sum of the maximum widths W1, W2, W3, W4 of the four teeth is 28.0 mm to 38 mm.

<A Set of Artificial Teeth of Maxillary Molar Teeth>

FIG. 17(b) shows a set of artificial teeth of maxillary molar teeth. In the figure, the left side is the distal side, the right side is the mesial side, the upside is the buccal side, and the downside is the lingual side.

The set of artificial teeth of maxillary molar teeth has the artificial teeth composed of a maxillary first premolar tooth 50, a maxillary second premolar tooth 60, a maxillary first molar tooth 70, and a maxillary second molar tooth 80.

The maximum width W6 of the artificial tooth of the maxillary second premolar tooth 60 is 85 to 95% of the maximum width W5 of the artificial tooth of the maxillary first premolar tooth 50.

The maximum width W7 of the artificial tooth of the maxillary first molar tooth 70 is 128 to 138% of the maximum width W5 of the artificial tooth of the maxillary first premolar tooth 50.

The maximum width W8 of the artificial tooth of the maxillary second molar tooth 80 is 163 to 173% of the maximum width W5 of the artificial tooth of the maxillary first premolar tooth 50.

The sum of the maximum widths W5, W6, W7, W8 of the four teeth is 26.0 mm to 36 mm.

<A Set of Artificial Teeth of Mandibular Posterior Teeth and Maxillary Posterior Teeth>

FIG. 18 shows a set of artificial teeth of mandibular posterior teeth and maxillary posterior teeth. In the figure, the left side is the distal side, the right side is the mesial side, the upside and downside are the buccal side, and the middle is the lingual side.

The set of artificial teeth of mandibular posterior teeth and maxillary posterior teeth is composed of a set of artificial teeth of mandibular posterior teeth 10, 20, 30, 40 and a set of artificial teeth of maxillary posterior teeth 50, 60, 70, 80.

The sum SW2 of the maximum widths W5, W6, W7, W8 of the set of the artificial teeth of the maxillary posterior teeth 50, 60, 70, 80 is 92 to 102% of the sum. SW1 of the maximum widths W1, W2, W3, W4 of the set of the artificial teeth of the mandibular posterior teeth 10, 20, 30, 40.

Materials used for the artificial teeth of the embodiment are properly selected from ceramic materials such as feldspar, quartz, and silica, or composite resins composed of resin components such as MMA, UDMA, EDMA, Bis-GMA, and organic or inorganic filler, and acrylic resin, and other resin materials usually employed in the dental industry.

Furthermore, to enhance the aesthetic effects, it is preferred to mold by laminating into a plurality of layers by using materials of two or more different colors at least for the enamel layer and the dental layer. The materials may be selected from those shown above, and two different materials of different colors may be prepared to combine for molding, or same materials of different colors may be prepared to use.

The molding method may be properly selected from methods of compression molding, injection molding, and injection-compression molding.

In the set of artificial teeth having such structure, the azimuth from the origin of each artificial tooth, the ratio of distance from the origin to the mesial surface, distal surface, buccal surface and the lingual surface, and the relative positions of the cusps and the pits are appropriately set, and also the occlusal contact relation between the pits and cusps of the mandibular molar artificial teeth and maxillary artificial teeth, the maximum width of each artificial tooth, and the sum of the maximum width of the set of artificial teeth of maxillary molar teeth to the set of artificial teeth of mandibular molar teeth are properly set. Accordingly, as shown in FIG. 19, when the artificial teeth of the mandibular molar teeth are arranged without gap on the plaster model, and each pair of opposite artificial teeth can be positioned in correct occlusion of the maxillary molar teeth on the artificial teeth of the mandibular molar teeth, the artificial teeth of adjacent maxillary molar teeth will not interfere with each other or spaced from each other. Therefore, in the set of artificial teeth of this positional relation, the denture of a specific occlusal state can be manufactured efficiently in a short time, and the labor is saved in the occlusion adjusting work after installation of the denture.

INDUSTRIAL APPLICABILITY

The present invention relates to an artificial tooth used in a plate denture manufactured in prosthetic dental treatment, and is used by a dental technician for manufacturing a denture.

The artificial tooth is a medical apparatus, and is presented in plural forms and sizes and various color, and a proper artificial tooth is selected by the dental technician or dentist among them.

The artificial tooth of the present invention may be used as an educational tool, for learning or training of denture arrangement or occlusion adjustment.

The invention claimed is:

1. A set of artificial teeth comprising:
an artificial tooth of a mandibular first premolar tooth (10) having a buccal cusp tip (11), a lingual cusp tip (12), a mesial pit (13a), and a distal pit (13b), wherein,
 a) with the distal pit (13b) being an origin of XYZ orthogonal coordinates of this tooth (10), an arrangement is determined such that (i) a line segment connecting between a point (M1a) for internally dividing a line segment connecting between the mesial pit (13a) and the distal pit (13b) by 29:71 and a point (M1b) for internally dividing a line segment connecting between the buccal cusp tip (11) and the lingual cusp tip (12) by 47:53 is parallel to the Z-axis, (ii) a line segment connecting between the mesial pit (13a) and the distal pit (13b) is parallel to the XZ plane of the XYZ orthogonal coordinates, and (iii) an X-coordinate value of the mesial pit (13a) is less than an X-coordinate value of the distal pit (13b),
 b) a ratio of a distance, measured along the X-axis, from the distal pit (13b) to a mesial surface (14a) of the tooth (10) which is at a minimum position of the X-coordinate value of the tooth (10), to a distance, measured along the X-axis, from the distal pit (13b) to a distal surface (14b) of the tooth (10) which is at a maximum position of X-coordinate value of the tooth (10) is 75:25 to 85:15, c) a ratio of a distance, measured along the Y-axis, from the distal pit (13b) to a buccal surface (14c) of the tooth (10) which is at a maximum position of Y-coordinate value of the tooth (10), to a distance, measured along the Y-axis, from the distal pit (13b) to a lingual surface (14d) of the tooth (10) which is at a minimum position of Y-coordinate value of the tooth (10) is 49:51 to 59:41, d) a distance (S1) between the mesial pit (13a) and the distal pit (13b) is 42 to 52% of the maximum width (W1) of the tooth (10), e1) a distance between the mesial pit (13a) and the buccal cusp tip (11) is 84 to 94% of the distance (S1) between the mesial pit (13a) and the distal pit (13b), e2) a distance between the mesial pit (13a) and the lingual cusp tip (12) is 66 to 76% of the distance (S1) between the mesial pit (13a) and the distal pit (13b), f1) a distance between the distal pit (13b) and the buccal cusp tip (11) is 110 to 120% of the distance (S1) between the mesial pit (13a) and the distal pit (13b), f2) a distance between the distal pit (13b) and the lingual cusp tip (12) is 83 to 93% of the distance (S1) between the mesial pit (13a) and the distal pit (13b), and g) a distance between the buccal cusp tip (11) and the lingual cusp tip (12) is 88 to 98% of the distance (S1) between the mesial pit (13a) and the distal pit (13b); and an opposing artificial tooth of a maxillary first premolar tooth (50) having a buccal cusp tip (51), a lingual cusp tip (52), a mesial pit (53a), and a distal pit (53b), wherein, a) with the lingual cusp tip (52) being an origin of XYZ orthogonal coordinates of this tooth (50), an arrangement is determined such that (i) a line segment connecting between a point (M5a) for internally dividing a line segment connecting between the mesial pit (53a) and the distal pit (53b) by 47:53 and a point (M5b) for internally dividing a line segment connecting between the buccal cusp tip (51) and the lingual cusp tip (52) by 55:45 is parallel to the Z-axis, (ii) a line segment connecting between the mesial pit (53a) and the distal pit (53b) is parallel to the XZ plane of the XYZ orthogonal coordinates, and (iii) an X-coordinate value of the mesial pit (53a) is greater than an X-coordinate value of the distal pit (53b), b) a ratio of a distance, measured along the X-axis, from the lingual cusp tip (52) to a mesial surface (54a) of the tooth (50) which is at a maximum position of X-coordinate value of the tooth (50), to a distance, measured along the X-axis, from the lingual cusp tip (52) to a distal surface (54b) of the tooth (50) which is at a minimum position of X-coordinate value of the tooth (50) is 37:63 to 47:53, c) a ratio of a distance, measured along the Y-axis, from the lingual cusp tip (52) to a lingual surface (54d) of the tooth (50) which is at a minimum position of Y-coordinate value of the tooth (50), to a distance, measured along the Y-axis, from the lingual cusp tip (52) to a buccal surface (54c) of the tooth (50) which is at a maximum position of Y-coordinate value of the tooth (50) is 79:21 to 89:11, d) a distance (S5) between the mesial pit (53a) and the distal pit (53b) is 36 to 46% of a maximum width (W5) of the tooth (50), e1) a distance between the mesial pit (53a) and the buccal cusp tip (51) is 147 to 157% of the distance (S5) between the mesial pit (53a) and the distal pit (53b), e2) a distance between the mesial pit (53a) and the lingual cusp tip (52) is 98 to 108% of the distance (S5) between the mesial pit (53a) and the distal pit (53b), f1) a distance between the distal pit (53b) and the buccal cusp tip (51) is 134 to 144% of the distance (S5) between the mesial pit (53a) and the distal pit (53b), f2) a distance between the distal pit (53b) and the lingual cusp tip (52) is 119 to 129% of the distance (S5) between the mesial pit (53a) and the distal pit (53b), and g) a distance between the buccal cusp tip (51) and the lingual cusp tip (52) is 185 to 195% of the distance (S5) between the mesial pit (53a) and the distal pit (53b);

wherein the following contacts are made at the same time,
an occlusal surface surrounding the distal pit (13b) of the artificial tooth of the mandibular first premolar tooth (10) contacts, at least at one contact point, with an occlusal surface surrounding the lingual cusp tip (52) of the artificial tooth of the maxillary first premolar tooth (50), and a buccal cusp tip outer bevel surrounding the buccal cusp tip (11) of the artificial tooth of the mandibular first premolar tooth (10) contacts, at least at one contact point, with a buccal inner bevel of the occlusal surface surrounding the mesial pit (53a) of the artificial tooth of the maxillary first premolar tooth (50); and wherein the artificial tooth of the mandibular first premolar tooth (10) is implemented in a mandibular first premolar location within a complete mandibular denture, and the artificial tooth of the maxillary first premolar tooth (50) is implemented in a maxillary first premolar location within a complete maxillary denture.

2. The set of artificial teeth according to claim 1,
wherein the occlusal surface is within 1.50 mm in radius from the distal pit (13b) of the artificial tooth of the mandibular first premolar tooth (10), and the occlusal surface is within 1.50 mm in radius from the lingual cusp tip (52) of the artificial tooth of the maxillary first premolar tooth (50); and wherein the buccal cusp tip outer bevel is within 1.50 mm in radius from the buccal cusp tip (11) of the artificial tooth of the mandibular first premolar tooth (10), and the buccal inner bevel of the occlusal surface is within 1.50 mm in radius from the mesial pit (53a) of the artificial tooth of the maxillary first premolar tooth (50).

3. A set of artificial teeth comprising:
an artificial tooth of a mandibular second premolar tooth (20) having a buccal cusp tip (21), a lingual cusp tip (22), a mesial pit (23a), and a distal pit (23b), wherein, a) with the distal pit (23b) being an origin of XYZ orthogonal coordinates of this tooth (20), an arrangement is determined such that (i) a line segment connecting between a point (M2a) for internally dividing a line segment connecting between the mesial pit (23a) and the distal pit (23b) by 21:79 and a point (M2b) for internally dividing a line segment connecting between the buccal cusp tip (21) and the lingual cusp tip (22) by 40:60 is parallel to the Z-axis, (ii) a line segment connecting between the mesial pit (23a)

and the distal pit (23b) is parallel to the XZ plane of the XYZ orthogonal coordinates, and (iii) an X-coordinate value of the mesial pit (23a) is less than an X-coordinate value of the distal pit (23b),
- b) a ratio of a distance, measured along the X-axis, from the distal pit (23b) to a mesial surface (24a) of the tooth (20) which is at a minimum position of X-coordinate value of the tooth (20), to a distance, measured along the X-axis, from the distal pit (23b) to a distal surface (24b) of the tooth (20) which is at a maximum position of X-coordinate value of the tooth (20) is 66:34 to 76:24,
- c) a ratio of a distance, measured along the Y-axis, from the distal pit (23b) to a buccal surface (24c) of the tooth (20) which is at a maximum position of Y-coordinate value of the tooth (20), to a distance, measured along the Y-axis, from the distal pit (23b) to a lingual surface (24d) of the tooth (20) which is at a minimum position of Y-coordinate value of the tooth (20) is 51:49 to 61:39,
- d) a distance (S2) between the mesial pit (23a) and the distal pit (23b) is 56 to 66% of a maximum width (W2) of the tooth (20),
- e1) a distance between the mesial pit (23a) and the buccal cusp tip (21) is 79 to 89% of the distance (S2) between the mesial pit (23a) and the distal pit (23b),
- e2) a distance between the mesial pit (23a) and the lingual cusp tip (22) is 88 to 98% of the distance (S2) between the mesial pit (23a) and the distal pit (23b),
- f1) a distance between the distal pit (23b) and the buccal cusp tip (21) is 97 to 107% of the distance (S2) between the mesial pit (23a) and the distal pit (23b),
- f2) a distance between the distal pit (23b) and the lingual cusp tip (22) is 127 to 137% of the distance (S2) between the mesial pit (23a) and the distal pit (23b), and
- g) a distance between the buccal cusp tip (21) and the lingual cusp tip (22) is 126 to 136% of the distance (S2) between the mesial pit (23a) and the distal pit (23b); and an opposing artificial tooth of a maxillary second premolar tooth (60) having a buccal cusp tip (61), a lingual cusp tip (62), a mesial pit (63a), and a distal pit (63b), wherein,
- a) with the lingual cusp tip (62) being an origin of XYZ orthogonal coordinates of this tooth (60), an arrangement is determined as such that (i) a line segment connecting between a point (M6a) for internally dividing a line segment connecting between the mesial pit (63a) and the distal pit (63b) by 54:46 and a point (M6b) for internally dividing a line segment connecting between the buccal cusp tip (61) and the lingual cusp tip (62) by 53:47 is parallel to the Z-axis, (ii) a line segment connecting between the distal pit (63b) and the mesial pit (63a) is parallel to the XZ plane of the XYZ orthogonal coordinates, and (iii) an X-coordinate value of the mesial pit (63a) is greater than an X-coordinate value of the distal pit (63b),
- b) a ratio of a distance, measured along the X-axis, from the lingual cusp tip (62) to a mesial surface (64a) of the tooth (60) which is at a maximum position of X-coordinate value of the tooth (60), to a distance, measured along the X-axis, from the lingual cusp tip (62) to a distal surface (64b) of the tooth (60) which is at a minimum position of X-coordinate value of the tooth (60) is 42:68 to 52:58,
- c) a ratio of a distance, measured along the Y-axis, from the lingual cusp tip (62) to a buccal surface (64c) of the tooth (60) which is at a maximum position of Y-coordinate value of the tooth (60), to a distance, measured along the Y-axis, from the lingual cusp tip (62) to a lingual surface (64d) of the tooth (60) which is at a minimum position of Y-coordinate value of the tooth (60) is 79:21 to 89:11,
- d) a distance (S6) between the mesial pit (63a) and the distal pit (63b) is 40 to 50% of a maximum width (W6) of the tooth (60),
- e1) a distance between the mesial pit (63a) and the buccal cusp tip (61) is 150 to 160% of the distance (S6) between the mesial pit (63a) and the distal pit (63b),
- e2) a distance between the mesial pit (63a) and the lingual cusp tip (62) is 117 to 127% of the distance (S6) between the mesial pit (63a) and the distal pit (63b),
- f1) a distance between the distal pit (63b) and the buccal cusp tip (61) is 142 to 132% of the distance (S6) between the mesial pit (63a) and the distal pit (63b),
- f2) a distance between the distal pit (63b) and the lingual cusp tip (62) is 128 to 138% of the distance (S6) between the mesial pit (63a) and the distal pit (63b), and
- g) a distance between the buccal cusp tip (61) and the lingual cusp tip (62) is 204 to 214% of the distance (S6) between the mesial pit (63a) and the distal pit (63b);

wherein the following contacts are made at the same time,
- an occlusal surface surrounding the distal pit (23b) of the artificial tooth of the mandibular second premolar tooth (20) contacts, at least at one contact point, with an occlusal surface surrounding the lingual cusp tip (62) of the artificial tooth of the maxillary second premolar tooth (60), and
- a buccal cusp tip outer bevel surrounding the buccal cusp tip (21) of the artificial tooth of the mandibular second premolar tooth (20) contacts, at least at one contact point, with a buccal inner bevel of the occlusal surface surrounding the mesial pit (63a) of the artificial tooth of the maxillary second premolar tooth (60); and wherein the artificial tooth of the mandibular second premolar tooth (20) is implemented in a mandibular second premolar location within a complete mandibular denture, and the artificial tooth of the maxillary second premolar tooth (60) is implemented in a maxillary second premolar location within a complete maxillary denture.

4. The set of artificial teeth according to claim 3,
wherein the occlusal surface is within 1.50 mm in radius from the distal pit (23b) of the artificial tooth of the mandibular second premolar tooth (20), and the occlusal surface is within 1.50 mm in radius from the lingual cusp tip (62) of the artificial tooth of the maxillary second premolar tooth (60); and
wherein the buccal cusp tip outer bevel is within 1.50 mm in radius from the buccal cusp tip (21) of the artificial tooth of the mandibular second premolar tooth (20), and the buccal inner bevel of the occlusal surface is within 1.50 mm in radius from the mesial pit (63a) of the artificial tooth of the maxillary second premolar tooth (60).

5. A set of artificial teeth comprising:
an artificial tooth of a mandibular first molar tooth (30) having a mesial buccal cusp tip (31a), a distal buccal cusp tip (31b), a mesial lingual cusp tip (32a), a distal lingual cusp tip (32b), a mesial pit (33a), a distal pit (33b), and a central fossa (33c), wherein, a) with the central fossa (33c) being an origin of XYZ orthogonal coordinates of this tooth (30), an arrangement is determined such that (i) a line segment connecting between a point (M3a) for internally dividing a line segment connecting between the mesial pit (33a) and the distal pit (33b) by 49:51 and a point (M3b) for internally dividing a line segment connecting between the mesial buccal cusp tip (31a) and the distal lingual cusp tip (32b) by 54:46 is parallel to the Z-axis, (ii) a line segment connecting between the distal pit (33b) and the mesial pit (33a) is parallel to the XZ plane of the XYZ orthogonal coordinates, and (iii) an X-coordinate value of the mesial pit (33a) is less than an X-coordinate value of the distal pit (33b), b) a ratio of a distance, measured along the X-axis, from the central fossa (33c) to a mesial surface (34a) of the tooth (30) which is at a minimum position of X-coordinate value of the tooth (30), to a distance, measured along the X-axis, from the distal pit (33b) to a distal surface (34b) of the tooth (30) which is at a maximum position of X-coordinate value of the tooth (30) is 45:65 to 55:45, c) a ratio of a distance, measured along the Y-axis, from the central fossa (33c) to a buccal surface (34c) of the tooth (30) which is at a maximum position of Y-coordinate value of the tooth (30), to a distance, measured along the Y-axis, from the central fossa (33c) to a lingual surface (34d) of the tooth (30) which is at a minimum position of Y-coordinate value of the tooth (30) is 61:39 to 71:29, d) a distance (S3) between the mesial pit (33a) and the distal pit (33b) is 57 to 67% of the maximum width (W3) of the tooth (30), e1) a distance between the mesial pit (33a) and the central fossa (33c) is 49 to 59% of the distance (S3) between the mesial pit (33a) and the distal pit (33b), e2) a distance between the mesial pit (33a) and the mesial buccal cusp tip (31a) is 46 to 56% of the distance (S3) between the mesial pit (33a) and the distal pit (33b), e3) a distance between the mesial pit (33a) and the distal buccal cusp tip (31b) is 70 to 80% of the distance (S3) between the mesial pit (33a) and the distal pit (33b), e4) a distance between the mesial pit (33a) and the mesial lingual cusp tip (32a) is 37 to 47% of the distance (S3) between the mesial pit (33a) and the distal pit (33b), e5) a distance between the mesial pit (33a) and the distal lingual cusp tip (32b) is 90 to 100% of the distance (S3) between the mesial pit (33a) and the distal pit (33b), e6) a distance between the mesial pit (33a) and the distal cusp tip (31c) is 119 to 129% of the distance (S3) between the mesial pit (33a) and the distal pit (33b), e7) a distance between the distal pit (33b) and the central fossa (33c) is 42 to 52% of the distance (S3) between the mesial pit (33a) and the distal pit (33b), f1) a distance between the distal pit (33b) and the mesial buccal cusp tip (31a) is 103 to 113% of the distance (S3) between the mesial pit (33a) and the distal pit (33b), f2) a distance between the distal pit (33b) and the distal buccal cusp tip (31b) is 66 to 76% of the distance (S3) between the mesial pit (33a) and the distal pit (33b), f3) a distance between the distal pit (33b) and the mesial lingual cusp tip (32a) is 88 to 98% of the distance (S3) between the mesial pit (33a) and the distal pit (33b), f4) a distance between the distal pit (33b) and the distal lingual cusp tip (32b) is 42 to 52% of the distance (S3) between the mesial pit (33a) and the distal pit (33b), f5) a distance between the distal pit (33b) and the distal cusp tip (31c) is 41 to 51% of the distance (S3) between the mesial pit (33a) and the distal pit (33b), g1) a distance between the central fossa (33c) and the mesial buccal cusp tip (31a) is 68 to 78% of the distance (S3) between the mesial pit (33a) and the distal pit (33b), g2) a distance between the central fossa (33c) and the distal buccal cusp tip (31b) is 52 to 62% of the distance (S3) between the mesial pit (33a) and the distal pit (33b), g3) a distance between the central fossa (33c) and the mesial lingual cusp tip (32a) is 46 to 56% of the distance (S3) between the mesial pit (33a) and the distal pit (33b), g4) a distance between the central fossa (33c) and the distal lingual cusp tip (32b) is 44 to 54% of the distance (S3) between the mesial pit (33a) and the distal pit (33b), g5) a distance between the central fossa (33c) and the distal cusp tip (31c) is 73 to 83% of the distance (S3) between the mesial pit (33a) and the distal pit (33b), h1) a distance between the mesial buccal cusp tip (31a) and the distal buccal cusp tip (31b) is 43 to 53% of the distance (S3) between the mesial pit (33a) and the distal pit (33b), h2) a distance between the mesial buccal cusp tip (31a) and the mesial lingual cusp tip (32b) is 70 to 80% of the distance (S3) between the mesial pit (33a) and the distal pit (33b), h3) a distance between the mesial buccal cusp tip (31a) and the distal lingual cusp tip (32 b) is 106 to 116% of the distance (S3) between the mesial pit (33a) and the distal pit (33b), h4) a distance between the mesial buccal cusp tip (31a) and the distal cusp tip (31c) is 106 to 116% of the distance (S3) between the mesial pit (33a) and the distal pit (33b), i1) a distance between the distal buccal cusp tip (31b) and the mesial lingual cusp tip (32a) is 80 to 90% of the distance (S3) between the mesial pit (33a) and the distal pit (33b), i2) a distance between the distal buccal cusp tip (31b) and the distal lingual cusp tip (32b) is 81 to 91% of the distance (S3) between the mesial pit (33a) and the distal pit (33b), i3) a distance between the distal buccal cusp tip (31b) and the distal cusp tip (31c) is 58 to 68% of the distance (S3) between the mesial pit (33a) and the distal pit (33b), j1) a distance between the mesial lingual cusp tip (32a) and the distal lingual cusp tip (32b) is 64 to 74% of the distance (S3) between the mesial pit (33a) and the distal pit (33b), j2) a distance between the mesial lingual cusp tip (32a) and the distal cusp tip (31c) is 115 to 125% of the distance (S3) between the mesial pit (33a) and the distal pit (33b), k) a distance between the distal cusp tip (31c) and the distal lingual cusp tip (32b) is 72 to 82% of the distance (S3) between the mesial pit (33a) and the distal pit (33b); and an opposing artificial tooth of a maxillary first molar tooth (70) having a mesial buccal cusp tip (71a), a distal buccal cusp tip (71b), a mesial lingual cusp tip (72a), a distal lingual cusp tip (72b), a mesial pit (73a), a distal pit (73b), and a central fossa (73c), wherein, a) with the mesial lingual cusp tip (72a) being an origin of XYZ orthogonal coordinates of this tooth (70), an arrangement is determined such that (i) a line segment connecting between a point (M7a) for internally dividing a line segment connecting between the mesial pit (73a) and the distal pit (73b) by 46:54 and a point (M7b) for internally dividing a line segment connecting between the distal buccal cusp tip (71b) and the mesial lingual cusp tip (72a) by 58:42 is parallel to the Z-axis, (ii) a line segment connecting between the distal pit (73b) and the mesial pit (73a) is parallel to the XZ plane of the XYZ orthogonal coordinates, and (iii) an X-coordinate value of the mesial pit (73a) is greater than an X-coordinate value of the distal pit (73b), b) a ratio of a distance, measured along the X-axis, from the mesial lingual cusp tip (72a) to a mesial surface (74a) of the tooth (70) which is at a maximum position of X-coordinate value of the tooth (70), to a distance, measured along the X-axis, from the mesial lingual cusp tip (72a) to a distal surface (74b) of the tooth (70) which is at a minimum position of X-coordinate value of the tooth (70) is 22:78 to 32:68, c) a ratio of a distance, measured along the Y-axis, from the mesial lingual cusp tip (72a) to a buccal surface (74c) of the tooth (70) which is at a maximum position of Y-coordinate value of the tooth (70), to a distance, measured along the Y-axis, from the mesial lingual cusp tip (72a) to a lingual surface (74d) of the tooth (70) which is at a minimum position of Y-coordinate value of the tooth (70) is 76:24 to 86:14, d) a distance (S7) between the mesial pit (73a) and the distal pit (73b) is 57 to 67% of a maximum width (W7) of the tooth (70), e1) a distance between the mesial pit (73a) and the central fossa (73c) is 37 to 47% of the distance (S7) between the mesial pit (73a) and the distal pit (73b), e2) a distance between the mesial pit (73a) and the mesial buccal cusp tip (71a) is 78 to 88% of the distance (S7) between the mesial pit (73a) and the distal pit (73b), e3) a distance between the mesial pit (73a) and the distal buccal cusp tip (71b) is 111 to 121% of the distance (S7) between the mesial pit (73a) and the distal pit (73b), e4) a distance between the mesial pit (73a) and the mesial lingual cusp tip (72a) is 51 to 61% of the distance (S7) between the mesial pit (73a) and the distal pit (73b), e5) a distance between the mesial pit (73a) and the distal lingual cusp tip (72b) is 109 to 119% of the distance (S7) between the mesial pit (73a) and the distal pit (73b), f1) a distance between the distal pit (73b) and the central fossa (73c) is 56 to 66% of the distance (S7) between the mesial pit (73a) and the distal pit (73b), f2) a distance between the distal pit (73b) and the mesial buccal cusp tip (71a) is 128 to 138% of the distance (S7) between the mesial pit (73a) and the distal pit (73b), f3) a distance between the distal pit (73b) and the distal buccal cusp tip (71b) is 68 to 78% of the distance (S7) between the mesial pit (73a) and the distal pit (73b), f4) a distance between the distal pit (73b) and the mesial lingual cusp tip (72a) is 102 to 112% of the distance (S7) between the mesial pit (73a) and the distal pit (73b), f5) a distance between the distal pit (73b) and the distal lingual cusp tip (72b) is 58 to 68% of the distance (S7) between the mesial pit (73a) and the distal pit (73b), g1) a distance between the central fossa (73c) and the mesial buccal cusp tip (71a) is 82 to 92% of the distance (S7) between the mesial pit (73a) and the distal pit (73b), g2) a distance between the central fossa (73c) and the distal buccal cusp tip (71b) is 78 to 88% of the distance (S7) between the mesial pit (73a) and the distal pit (73b), g3) a distance between the central fossa (73c) and the mesial lingual cusp tip (72a) is 70 to 80% of the distance (S7) between the mesial pit (73a) and the distal pit (73b), g4) a distance between the central fossa (73c) and the distal lingual cusp tip (72b) is 88 to 98% of the distance (S7) between the mesial pit (73a) and the distal pit (73b), h1) a distance between the mesial buccal cusp tip (71a) and the distal buccal cusp tip (71b) is 90 to 100% of the distance (S7) between the mesial pit (73a) and the distal pit (73b), h2) a distance between the mesial buccal cusp tip (71a) and the mesial lingual cusp tip (72a) is 112 to 122% of the distance (S7) between the mesial pit (73a) and the distal pit (73b), h3) a distance between the mesial buccal cusp tip (71a) and the distal lingual cusp tip (72b) is 154 to 164% of the distance (S7) between the mesial pit (73a) and the distal pit (73b), i1) a distance between the distal buccal cusp tip (71b) and the mesial lingual cusp tip (72a) is 125 to 135% of the distance (S7) between the mesial pit (73a) and the distal pit (73b), i2) a distance between the distal buccal cusp tip (71b) and the distal lingual cusp tip (72b) is 106 to 116% of the distance (S7) between the mesial pit (73a) and the distal pit (73b), and j) a distance between the mesial lingual cusp tip (72a) and the distal lingual cusp tip (72b) is 81 to 91% of the distance (S7) between the mesial pit (73a) and the distal pit (73b);

wherein the following contacts are made at the same time, a first occlusal surface surrounding the central fossa (33c) of the artificial tooth of the mandibular first molar tooth (30) contacts, at least one contact point, with a second occlusal surface surrounding the mesial lingual cusp tip (72a) of the artificial tooth of the maxillary first molar tooth (70), a third occlusal surface surrounding the mesial buccal cusp tip (31a) of the artificial tooth of the mandibular first molar tooth (30) contacts, at least one contact point, with a fourth occlusal surface surrounding the mesial pit (73a) and located at an inner bevel of the mesial buccal cusp tip (71a) of the artificial tooth of the maxillary first molar tooth (70), a fifth occlusal surface surrounding the distal buccal cusp tip (31b) of the artificial tooth of the mandibular first molar tooth (30) contacts, at least one contact point, with a sixth occlusal surface surrounding the central fossa (73c) and located at an inner bevel of the mesial buccal cusp tip (71a) of the artificial tooth of the maxillary first molar tooth (70), a seventh occlusal surface surrounding the distal buccal cusp tip (31b) of the artificial tooth of the mandibular first molar tooth (30) contacts, at least one contact point, with an eighth occlusal surface surrounding the central fossa (73c) and located at an inner bevel of the distal buccal cusp tip (71b) of the artificial tooth of the maxillary first molar tooth (70), and a ninth occlusal surface surrounding the distal cusp tip (31c) of the artificial tooth of the mandibular first molar tooth (30) contacts, at least one contact point, with a tenth occlusal surface surrounding the distal pit (73b) and located at an inner bevel of the distal buccal cusp tip (71b) of the artificial tooth of the maxillary first molar tooth (70); and wherein the artificial tooth of the mandibular first molar tooth (30) is implemented in a mandibular first molar location within a complete mandibular denture, and the artificial tooth of the maxillary first molar tooth (70) is implemented in a maxillary first molar location within a complete maxillary denture.

6. The set of artificial teeth according to claim 5, wherein the first occlusal surface is within 1.50 mm in radius from the central fossa (33c) of the artificial tooth of the mandibular first molar tooth (30), and the second occlusal surface is within 1.50 mm in radius from the mesial lingual cusp tip (72a) of the artificial tooth of the maxillary first molar tooth (70), wherein the third occlusal surface is within 1.50 mm in radius from the mesial buccal cusp tip (31a) of the artificial tooth of the mandibular first molar tooth (30), and the fourth occlusal surface is within 1.50 mm from the mesial pit (73a) of the inner bevel of the mesial buccal cusp tip (71a) of the artificial tooth of the maxillary first molar tooth (70), wherein the fifth occlusal surface is within 1.50 mm in radius from the distal buccal cusp tip (31b) of the artificial tooth of the mandibular first molar tooth (30), and the sixth occlusal surface is within 1.50 mm from the central fossa (73c) of the inner bevel of the mesial buccal cusp tip (71a) of the artificial tooth of the maxillary first molar tooth (70), wherein the seventh occlusal surface is within 1.50 mm in radius from the distal buccal cusp tip (31b) of the artificial tooth of the mandibular first molar tooth (30), and the eighth occlusal surface is within 1.50 mm from the central fossa (73c) of the inner bevel of the distal buccal cusp tip (71b) of the artificial tooth of the maxillary first molar tooth (70), and wherein the ninth occlusal surface is within 1.50 mm in radius from the distal cusp tip (31c) of the artificial tooth of the mandibular first molar tooth (30), and the tenth occlusal surface is within 1.50 mm from the distal pit (73b) of the inner bevel of the distal buccal cusp tip (71b) of the artificial tooth of the maxillary first molar tooth (70).

7. A set of artificial teeth comprising:

an artificial tooth of a mandibular second molar tooth (40) having a mesial buccal cusp tip (41a), a distal buccal cusp tip (41b), a mesial lingual cusp tip (42a), a distal lingual cusp tip (42b), a mesial pit (43a), a distal pit (43b), and a central fossa (43c), wherein, a) with the central fossa (43c) being an origin of XYZ orthogonal coordinates of this tooth (40), an arrangement is determined such that (i) a line segment connecting between a point (M4a) for internally dividing a line segment connecting between the mesial pit (43a) and the distal pit (43b) by 53:47 and a point (M4b) for internally dividing a line segment connecting between the mesial buccal cusp tip (41a) and the distal lingual cusp tip (42b) by 57:43 is parallel to the Z-axis, (ii) a line segment connecting between the distal pit (43b) and the mesial pit (43a) is parallel to the XZ plane of the XYZ orthogonal coordinates, and (iii) an X-coordinate value of the mesial pit (43a) is less than an X-coordinate value of the distal pit (43b), b) a ratio of a distance, measured along the X-axis, from the central fossa (43c) to a mesial surface (44a) of the tooth (40) which is at a minimum position of X-coordinate value of the tooth (40), to a distance, measured along the X-axis, from the central fossa (43c) to a distal surface (44b) of the tooth (40) which is at a maximum position of X-coordinate value of the tooth (40) is 40:60 to 50:50, c) a ratio of a distance, measured along the Y-axis, from the central fossa (43c) to a buccal surface (44c) of the tooth (40) which is at a maximum position of Y-coordinate value of the tooth (40), to a distance, measured along the Y-axis, from the central fossa (43c) to a lingual surface (44d) of the tooth (40) which is at a minimum position of Y-coordinate value of the tooth (40) is 56:44 to 66:34, d) a distance (S4) between the mesial pit (43a) and the distal pit (43b) is 56 to 66% of the maximum width (W4) of the tooth (40), e1) a distance between the mesial pit (43a) and the central fossa (43c) is 43 to 53% of the distance (S4) between the mesial pit (43a) and the distal pit (43b), e2) a distance between the mesial pit (43a) and the mesial buccal cusp tip (41a) is 58 to 68% of the distance (S4) between the mesial pit (43a) and the distal pit (43b), e3) a distance between the mesial pit (43a) and the distal buccal cusp tip (41b) is 99 to 108% of the distance (S4) between the mesial pit (43a) and the distal pit (43b), e4) a distance between the mesial pit (43a) and the mesial lingual cusp tip (42a) is 44 to 54% of the distance (S4) between the mesial pit (43a) and the distal pit (43b), e5) a distance between the mesial pit (43a) and the distal lingual cusp tip (42b) is 90 to 80% of the distance (S4) between the mesial pit (43a) and the distal pit (43b), f1) a distance between the distal pit (43b) and the central fossa (43c) is 48 to 58% of the distance (S4) between the mesial pit (43a) and the distal pit (43b), f2) a distance between the distal pit (43b) and the mesial buccal cusp tip (41a) is 102 to 112% of the distance (S4) between the mesial pit (43a) and the distal pit (43b), f3) a distance between the distal pit (43b) and the distal buccal cusp tip (41b) is 46 to 56% of the distance (S4) between the mesial pit (43a) and the distal pit (43b), f4) a distance between the distal pit (43*b*) and the mesial lingual cusp tip (42*a*) is 99 to 109% of the distance (S4) between the mesial pit (43*a*) and the distal pit (43*b*), f5) a distance between the distal pit (43*b*) and the distal lingual cusp tip (42*b*) is 42 to 52% of the distance (S4) between the mesial pit (43*a*) and the distal pit (43*b*), g1) a distance between the central fossa (43*c*) and the mesial buccal cusp tip (41*a*) is 70 to 80% of the distance (S4) between the mesial pit (43*a*) and the distal pit (43*b*), g2) a distance between the central fossa (43*c*) and the distal buccal cusp tip (41*b*) is 64 to 74% of the distance (S4) between the mesial pit (43*a*) and the distal pit (43*b*), g3) a distance between the central fossa (43*c*) and the mesial lingual cusp tip (42*a*) is 57 to 67% of the distance (S4) between the mesial pit (43*a*) and the distal pit (43*b*), g4) a distance between the central fossa (43*c*) and the distal lingual cusp tip (42*b*) is 52 to 62% of the distance (S4) between the mesial pit (43*a*) and the distal pit (43*b*), h1) a distance between the mesial buccal cusp tip (41*a*) and the distal buccal cusp tip (41*b*) is 74 to 84% of the distance (S4) between the mesial pit (43*a*) and the distal pit (43*b*), h2) a distance between the mesial buccal cusp tip (41*a*) and the mesial lingual cusp tip (42*a*) is 89 to 99% of the distance (S4) between the mesial pit (43*a*) and the distal pit (43*b*), h3) a distance between the mesial buccal cusp tip (41*a*) and the distal lingual cusp tip (42*b*) is 113 to 123% of the distance (S4) between the mesial pit (43*a*) and the distal pit (43*b*), i1) a distance between the distal buccal cusp tip (41*b*) and the mesial lingual cusp tip (42*a*) is 112 to 122% of the distance (S4) between the mesial pit (43*a*) and the distal pit (43*b*), i2) a distance between the distal buccal cusp tip (41*b*) and the distal lingual cusp tip (42*b*) is 79 to 89% of the distance (S4) between the mesial pit (43*a*) and the distal pit (43*b*), and j) a distance between the mesial lingual cusp tip (42*a*) and the distal lingual cusp tip (42*b*) is 71 to 81% of the distance (S4) between the mesial pit (43*a*) and the distal pit (43*b*); and an opposing artificial tooth of a maxillary second molar tooth (80) having a mesial buccal cusp tip (81*a*), a distal buccal cusp tip (81*b*), a mesial lingual cusp tip (82*a*), a distal lingual cusp tip (82*b*), a mesial pit (83*a*), a distal pit (83*b*), and a central fossa (83*c*), wherein, a) with the mesial lingual cusp tip (82*a*) being an origin of XYZ orthogonal coordinates of this tooth (80), an arrangement is determined as such that (i) a line segment connecting between a point (M8*a*) for internally dividing a line segment connecting between the mesial pit (83*a*) and the distal pit (83*b*) by 78:22 and a point (M8*b*) for dividing a line segment connecting between the distal buccal cusp tip (81*b*) and the mesial lingual cusp tip (82*a*) by 30:70 is parallel to the Z-axis, (ii) a line segment connecting between the distal pit (83*b*) and the mesial pit (83*a*) is parallel to the XZ plane of the XYZ orthogonal coordinates, and (iii) an X-coordinate value of the mesial pit (83*a*) is greater than an X-coordinate value of the distal pit (83*b*), b) a ratio of a distance, measured along the X-axis, from the mesial lingual cusp tip (82*a*) to a mesial surface (84*a*) of the tooth (80) which is at a maximum position of X-coordinate value of the tooth (80), to a distance, measured along the X-axis, from the mesial lingual cusp tip (82*a*) to a distal surface (84*b*) of the tooth (80) which is at a minimum position of X-coordinate value of the tooth (80) is 32:68 to 42:58, c) a ratio of a distance, measured along the Y-axis, from the mesial lingual cusp tip (82*a*) to a buccal surface (84*c*) of the tooth (80) which is at a maximum position of Y-coordinate value of the tooth (80), to a distance, measured along the Y-axis, from the mesial lingual cusp tip (82*a*) to a lingual surface (84*d*) of the tooth (80) which is at a minimum position of Y-coordinate value of the tooth (80) is 85:15 to 95:5, d) a distance (S8) between the mesial pit (83*a*) and the distal pit (83*b*) is 40 to 50% of the maximum width (W8) of the tooth (80), e1) a distance between the mesial pit (83*a*) and the central fossa (83*c*) is 42 to 52% of the distance (S8) between the mesial pit (83*a*) and the distal pit (83*b*), e2) a distance between the mesial pit (83*a*) and the mesial buccal cusp tip (81*a*) is 58 to 68% of the distance (S8) between the mesial pit (83*a*) and the distal pit (83*b*), e3) a distance between the mesial pit (83*a*) and the distal buccal cusp tip (81*b*) is 101 to 111% of the distance (S8) between the mesial pit (83*a*) and the distal pit (83*b*), e4) a distance between the mesial pit (83*a*) and the mesial lingual cusp tip (82*a*) is 65 to 75% of the distance (S8) between the mesial pit (83*a*) and the distal pit (83*b*), e5) a distance between the mesial pit (83*a*) and the distal lingual cusp tip (82*b*) is 102 to 112% of the distance (S8) between the mesial pit (83*a*) and the distal pit (83*b*), f1) a distance between the distal pit (83*b*) and the central fossa (83*c*) is 49 to 59% of the distance (S8) between the mesial pit (83*a*) and the distal pit (83*b*), f2) a distance between the distal pit (83*b*) and the mesial buccal cusp tip (81*a*) is 103 to 113% of the distance (S8) between the mesial pit (83*a*) and the distal pit (83*b*), f3) a distance between the distal pit (83*b*) and the distal buccal cusp tip (81*b*) is 37 to 47% of the distance (S8) between the mesial pit (83*a*) and the distal pit (83*b*), f4) a distance between the distal pit (83*b*) and the mesial lingual cusp tip (82*a*) is 94 to 104% of the distance (S8) between the mesial pit (83*a*) and the distal pit (83*b*), f5) a distance between the distal pit (83*b*) and the distal lingual cusp tip (82*b*) is 46 to 56% of the distance (S8) between the mesial pit (83*a*) and the distal pit (83*b*), g1) a distance between the central fossa (83*c*) and the mesial buccal cusp tip (81*a*) is 70 to 80% of the distance (S8) between the mesial pit (83*a*) and the distal pit (83*b*), g2) a distance between the central fossa (83*c*) and the distal buccal cusp tip (81*b*) is 65 to 75% of the distance (S8) between the mesial pit (83*a*) and the distal pit (83*b*), g3) a distance between the central fossa (83*c*) and the mesial lingual cusp tip (82*a*) is 68 to 78% of the distance (S8) between the mesial pit (83*a*) and the distal pit (83*b*), g4) a distance between the central fossa (83*c*) and the distal lingual cusp tip (82*b*) is 68 to 78% of the distance (S8) between the mesial pit (83*a*) and the distal pit (83*b*), h1) a distance between the mesial buccal cusp tip (81*a*) and the distal buccal cusp tip (81*b*) is 85 to 95% of the distance (S8) between the mesial pit (83*a*) and the distal pit (83*b*), h2) a distance between the mesial buccal cusp tip (81*a*) and the mesial lingual cusp tip (82*a*) is 102 to 112% of the distance (S8) between the mesial pit (83*a*) and the distal pit (83*b*), h3) a distance between the mesial buccal cusp tip (81*a*) and the distal lingual cusp tip (82*b*) is 122 to 132% of the distance (S8) between the mesial pit (83*a*) and the distal pit (83*b*), i1) a distance between the distal buccal cusp tip (81*b*) and the mesial lingual cusp tip (82*a*) is 107 to 117% of the distance (S8) between the mesial pit (83*a*) and the distal pit (83*b*), i2) a distance between the distal buccal cusp tip (81*b*) and the distal lingual cusp tip (82*b*) is 70 to 80% of the distance (S8) between the mesial pit (83*a*) and the distal pit (83*b*), and j) a distance between the mesial lingual cusp tip (82*a*) and the distal lingual cusp tip (82*b*) is 65 to 75% of the distance (S8) between the mesial pit (83*a*) and the distal pit (83*b*);

wherein the following contacts are made at the same time, a first occlusal surface surrounding the central fossa (43*c*) of the artificial tooth of the mandibular second molar tooth (40) contacts, at least one contact point, with a second occlusal surface surrounding the mesial lingual cusp tip (82*a*) of the artificial tooth of the maxillary second molar tooth (80), a third occlusal surface surrounding the mesial buccal cusp tip (41*a*) of the artificial tooth of the mandibular second molar tooth (40) contacts, at least one contact point, with a fourth occlusal surface surrounding the mesial pit (83*a*) and located at an inner bevel of the mesial buccal cusp tip (81*a*) of the artificial tooth of the maxillary second molar tooth (80), a fifth occlusal surface surrounding the distal buccal cusp tip (41*b*) of the artificial tooth of the mandibular second molar tooth (40) contacts, at least one contact point, with a sixth occlusal surface surrounding the central fossa (83*c*) and located at an inner bevel of the mesial buccal cusp tip (81*a*) of the artificial tooth of the maxillary second molar tooth (80), and a seventh occlusal surface surrounding the distal buccal cusp tip (41*b*) of the artificial tooth of the mandibular second molar tooth (40) contacts, at least one contact point, with an eighth occlusal surface surrounding the central fossa (83*c*) and located at an inner bevel of the distal buccal cusp tip (81*b*) of the artificial tooth of the maxillary second molar tooth (80); and wherein the artificial tooth of the mandibular second molar tooth (40) is implemented in a mandibular second molar location within a complete mandibular denture, and the artificial tooth of the maxillary second molar tooth (80) is implemented in a maxillary second molar location within a complete maxillary denture.

8. The set of artificial teeth according to claim 7, wherein the first occlusal surface is within 1.50 mm in radius from the central fossa (43*c*) of the artificial tooth of the mandibular second molar tooth (40), and the second occlusal surface is within 1.50 mm in radius from the mesial lingual cusp tip (82*a*) of the artificial tooth of the maxillary second molar tooth (80), wherein the third occlusal surface is within 1.50 mm in radius from the mesial buccal cusp tip (41*a*) of the artificial tooth of the mandibular second molar tooth (40), and the fourth occlusal surface is within 1.50 mm from the mesial pit (83*a*) of the inner bevel of the mesial buccal cusp tip (81*a*) of the artificial tooth of the maxillary second molar tooth (80), wherein the fifth occlusal surface is within 1.50 mm in radius from the distal buccal cusp tip (41*b*) of the artificial tooth of the mandibular second molar tooth (40), and the sixth occlusal surface is within 1.50 mm from the central fossa (83*c*) of the inner bevel of the mesial buccal cusp tip (81*a*) of the artificial tooth of the maxillary second molar tooth (80), and wherein the seventh occlusal surface is within 1.50 mm in radius from the distal buccal cusp tip (41*b*) of the artificial tooth of the mandibular second molar tooth (40), and the eighth occlusal surface is within 1.50 mm from the central fossa (83*c*) of the inner bevel of the distal buccal cusp tip (81*b*) of the artificial tooth of the maxillary second molar tooth (80).

* * * * *